United States Patent
Majeed et al.

(10) Patent No.: US 9,387,193 B2
(45) Date of Patent: *Jul. 12, 2016

(54) COMPOSITION COMPRISING SCIRPUSIN A AND SCIRPUSIN B AND ANTI-ADIPOGENESIS/ANTI-OBESITY POTENTIAL THEREOF

(71) Applicants: Muhammed Majeed, Edison, NJ (US); Kalyanam Nagabhushanam, East Windsor, NJ (US); Douglas Kalman, Weston, FL (US); Beena Bhat, Bangalore (IN); Priti Vaidyanathan, Bangalore (IN); Sarang Bani, Bangalore (IN); Anjali Pandey, Bangalore (IN)

(72) Inventors: Muhammed Majeed, Edison, NJ (US); Kalyanam Nagabhushanam, East Windsor, NJ (US); Douglas Kalman, Weston, FL (US); Beena Bhat, Bangalore (IN); Priti Vaidyanathan, Bangalore (IN); Sarang Bani, Bangalore (IN); Anjali Pandey, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 77 days.

This patent is subject to a terminal disclaimer.

(21) Appl. No.: 13/944,634

(22) Filed: Jul. 17, 2013

(65) Prior Publication Data

US 2014/0024706 A1  Jan. 23, 2014

Related U.S. Application Data

(60) Provisional application No. 61/672,849, filed on Jul. 18, 2012.

(51) Int. Cl.
*A61K 31/343* (2006.01)
*A61K 36/8905* (2006.01)

(52) U.S. Cl.
CPC .......... *A61K 31/343* (2013.01); *A61K 36/8905* (2013.01)

(58) Field of Classification Search
CPC .............. A61K 31/05; A61K 2300/00; A61K 2201/09; C07D 307/80
USPC .......................................... 435/375; 426/648
See application file for complete search history.

(56) References Cited

U.S. PATENT DOCUMENTS

2012/0128808 A1* 5/2012 Gokaraju et al. ............. 424/777

OTHER PUBLICATIONS

Bernard Lemaure, André Touché, Irène Zbinden, Julie Moulin, Didier Courtois, Katherine Macé and Christian Darimont, Administration of Cyperus rotundus Tubers Extract prevents Weight Gain in Obese Zucker rats, Phytother. Res. 21, 724-730 (2007).*
Kaoru Nakajima, Heihachiro Taguchi, Tohru Endo, and Itiro Yosioka, The Constituents of Scirpus fluviatilis(Torr.) A . Gray. I. The Structures of Two New Hydroxystilbene Dimers, Scirpusin A and B, Chem. Pharm. Bull., 26(10), 3050-3057, (1978).*

* cited by examiner

*Primary Examiner* — Sarah Pihonak
*Assistant Examiner* — Jason A Deck

(57) ABSTRACT

Disclosed is a composition comprising scirpusin A and scirpusin B and anti-obesity potential thereof. Also disclosed are methods of inhibiting adipogenesis using a composition comprising scirpusin A and scirpusin B. The present invention also disclosed methods of therapeutically managing obesity in mammals using a composition comprising scirpusin A and scirpusin B. Still further, the present invention also relates to a method of obtaining compositions comprising A. scirpusin A and scirpusin B and B. piceatannol and its dimers scirpusin A and scirpusin B through bioactivity guided fractionation of the rhizomes of *Cyperus rotundus*.

4 Claims, 10 Drawing Sheets

COMPOSITION COMPRISING SCIRPUSIN A AND SCIRPUSIN B AND ANTI-ADIPOGENESIS/ANTI-OBESITY POTENTIAL THEREOF

This application is non-provisional filing of provisional application No. 61/672,849 filed on 18 Jul. 2012, the contents of which are incorporated herein by reference.

BACKGROUND OF THE INVENTION

1. Field of the Invention

The invention in general pertains to compositions for adipogenesis inhibition. More specifically, the present invention discloses a composition comprising scirpusin A and scirpusin B and anti-adipogenesis/anti-obesity potential thereof.

2. Description of Prior Art

Scirpusin A as a hydroxystilbene dimer from Xinjiang wine grape has been previously reported by Kong Q et al in J Sci Food Agric. 2010 Apr. 15; 90(5):823-8. Scirpusin A has been noted for its amyloid-beta-peptide aggregation inhibitory activity (Rivière C et al (2010)), singlet oxygen quenching and DNA protective activity (Kong Q et al (2010)) and beta-secretase inhibitory activity (Jeon S Y et al (2007)).

Scirpusin B is a well established vaso-relaxing dimer of piceatannol and has been obtained in large amounts from passion fruit (Sano S et al, "Identification of the strong vaso-relaxing substance scirpusin B, a dimer of piceatannol, from passion fruit (*Passiflora edulis*) seeds, J Agric Food Chem. 2011 Jun. 8; 59(11):6209-13. Scirpusin B is also noted for its mild GSH activity (Maruki-Uchida H et al (2013)) and anti-HIV properties (Yang G X et al (2005)).

It has been previously reported that hexane extract of *Cyperus rotundus* tuber extracts exhibit anti-obesity properties. (Administration of *Cyperus rotundus* rhizomes extract prevents Weight Gain in Obese Zucker rats. Lemaure et al. 2007. Phytother Res. 21: 724-730.). The hexane fraction has been characterized to contain α-Cypernone, Rotundene, β-selinene, Calamenene, Cyperene, d-cadinene, Cyperotundone, Cadalene, Patchoulenone, Nootkatene, Sugeonol, g-calacorene, Kobusone, Cyperol, Isokobusone and Epi-a-selinene (Yadav et al. International Journal of Pharmaceutical and Clinical Research 2010; 2(1): 20-22). But the present invention discloses anti-obesity activity in ethyl acetate fraction of *Cyperus rotundus* This ethyl acetate fraction does not contain any of the many constituents of the hexane fraction. The present ethyl acetate fraction contains stilbenoid derived compounds, a class of compounds not reported to be occurring *Cyperus rotundus* by any investigator thus far. Hence it is the unique combination of the unexpected discovery of the occurrence of stilbenoid derived compounds and further their anti-obesity action. It is also a surprising finding that following the bioactivity guided fractionation of the rhizomes from *Cyperus rotundus*, a subfraction of ethyl acetate layer was characterized by the concentrated presence of two piceatannol dimers scirpusin A and scirpusin B which showed excellent anti-adipogenic effect in comparison to another subtraction that was concentrated with piceatannol along with dimers scirpusin A and scirpusin B. Thus the inventors of the present invention demonstrate for the first time the presence of scirpusin A and scirpusin B in the ethyl acetate fraction of the rhizomes *Cyperus rotundus* and anti-adipogenesis/anti-obesity potential thereof. comprising It is thus the principle objective of the present invention to disclose a composition scirpusin A and scirpusin B and anti-adipogenesis/anti-obesity potential thereof.

It is another objective of the present invention to disclose a method of inhibiting adipogenesis in mammalian cells using a composition comprising scirpusin A and scirpusin B.

It is yet another objective of the present invention to disclose a method of managing obesity in mammals using a composition comprising scirpusin A and scirpusin B.

It is a further objective of the present invention to disclose a method of obtaining compositions comprising A. scirpusin A and scirpusin B and B. piceatannol and its dimers scirpusin A and scirpusin B through bioactivity guided fractionation of the rhizomes of *Cyperus rotundus*.

The present invention fulfills the aforesaid objectives and provides further related advantages.

SUMMARY OF THE INVENTION

The present invention discloses compositions comprising scirpusin A and scirpusin B and anti-adipogenesis/anti-obesity potential thereof. The invention also discloses a method of managing obesity in mammals using a composition comprising scirpusin A and scirpusin B. The present invention further discloses a method of obtaining compositions comprising A. scirpusin A and scirpusin B and B. piceatannol and its dimers scirpusin A and scirpusin B through bioactivity guided fractionation of the rhizomes of *Cyperus rotundus*. Other features and advantages of the present invention will become apparent from the following more detailed description, taken in conjunction with the accompanying images, which illustrate, by way of example, the principle of the invention.

DETAILED DESCRIPTION OF THE DRAWINGS

DESCRIPTION OF THE MOST PREFERRED EMBODIMENT

Figure 1:
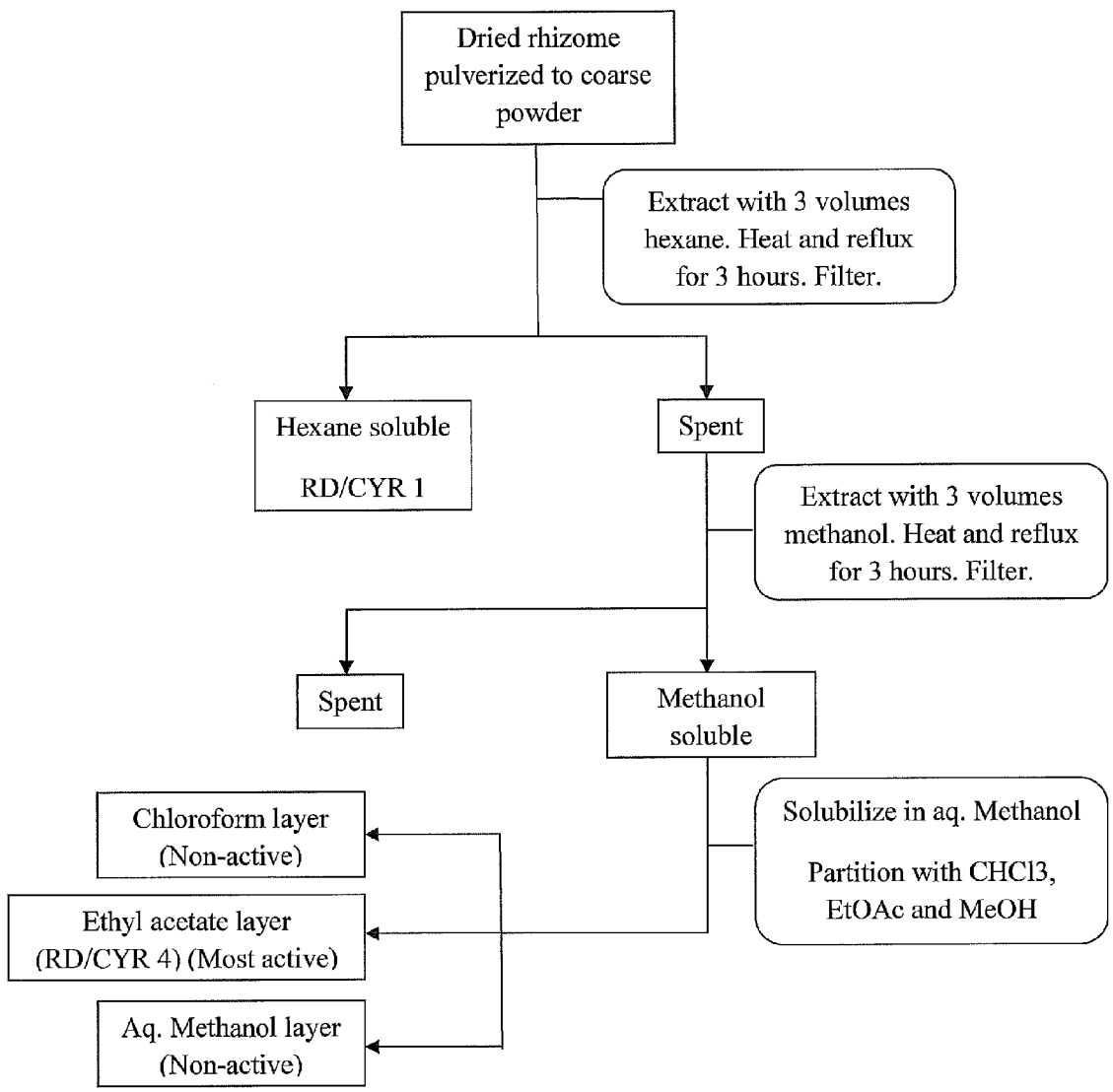
FIG. 1 shows a flowchart outlining the steps of extracting active principles from the rhizomes of *Cyperus rotundus*.

In the most preferred embodiment the present invention relates to anti-adipogenic/anti-obesity composition comprising scirpusin A and scirpusin B represented by STR#1 and STR#2 respectively.

In another most preferred embodiment, the present invention relates to a method of inhibiting adipogenesis in mammalian cells, said method comprising step of bringing to contact adipogenic mammalian cells with a composition comprising scirpusin A and scirpusin B represented by STR#1 and STR#2 respectively.

In another most preferred embodiment, the present invention relates to the method of therapeutically inhibiting obesity caused by adipogenesis in mammals, said method comprising step of dietary supplementation of a composition comprising scirpusin A and scirpusin B represented by STR#1 and STR#2 respectively to a mammal in need of said therapeutic inhibition.

In another most preferred embodiment, the present invention relates to the use of a composition comprising scirpusin A and scirpusin B represented by STR#1 and STR#2 for inhibiting adipogenesis in mammalian cells.

In an alternate embodiment, the present invention also relates to a process for the bioactivity guided fractionation of the rhizomes of *Cyperus rotundus* to obtain anti-adipogenic/anti-obesity compositions comprising A. scirpusin A and scirpusin B represented by STR#1 and STR#2 and B. piceatannol and its dimers scirpusin A and scirpusin B represented by STR#1 and STR#2 respectively, said process comprising the steps of:

1. Drying the rhizomes of *Cyperus rotundus* and pulverizing the same to form a coarse powder;
2. Extracting the powder of step 1 with 3 volumes of hexane followed by heating, reflux for 3 hours and filtering to obtain the hexane soluble fraction and spent material;
3. Extracting the spent material of step 2 with 3 volumes of methanol followed by heating, reflux for 3 hours and filtering to obtain the methanol soluble active fraction and spent material;
4. Solubilizing the methanol soluble active fraction of step 3 in aqueous methanol and successively partitioning with chloroform (CHCl3), Ethyl acetate (EtOAc) and methanol to obtain the chloroform layer, ethyl acetate layer and the aqueous methanol layer respectively.
5. Subjecting the chloroform layer, ethyl acetate layer and the aqueous methanol layer to further bioactivity guided fractionation, wherein the bioactivity parameter is the ability of the chloroform layer, ethyl acetate layer and the aqueous methanol layer to inhibit adipogenesis in 3T3-L1 mouse adipocytes (mammalian adipocytes).
6. Calculating the $IC_{50}$ (µg/ml) values for adipogenesis inhibition exemplified by chloroform layer, ethyl acetate layer and the aqueous methanol layer (0, 9.39 and 66.42 respectively).
7. Fractionation of the ethyl acetate layer using column fractionation to identify the bioactivity (adipogenesis inhibition) biomarker, said fractionation includes the step where fractions are eluted with increasing polarity of methanol: chloroform to yield sub-fractions of the ethyl acetate layer (fraction).
8. Subjecting the sub fractions of step 7 for bioactivity (anti-adipogenesis) analysis.
9. Identifying the most bioactive sub fractions of step 8 and subjecting the same to LC-MS analysis to identify the bioactive principles scirpusin A and scirpusin B;
10. Subjecting sub fractions of step 7 through the preparative HPLC to obtain purified dimer and subjecting the same to High Resolution Mass Spectroscopy (HRMS), liquid chromatography-mass spectrometry (LC-MS/MS) and Nuclear Magnetic Resonance Spectroscopy (NMR) to confirm the mass and structures of scirpusin bioactive principles.

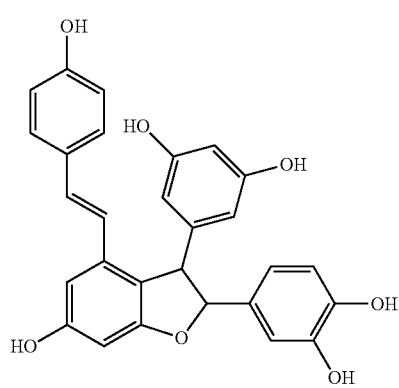

STR#1

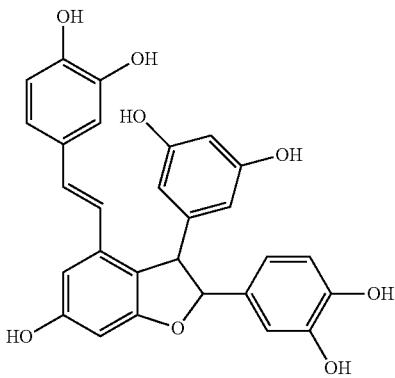

STR#2

The present inventors investigated the hexane extract referred in step 2 preceding and found that Scirpusin A & Scirpusin B were not present. Hence hexane extract in step 1 is constitutionally different from ethyl acetate fraction detailed in step 7. Thus the ethyl acetate extract of *Cyperus rotundus* is quite different from the hexane extract that was the subject of investigation in Lemaure et al. 2007. Phytother Res. 21: 724-730

The following sections of this specification consist of illustrative examples of the most preferred embodiments of the present invention.

Example 1

Bioactivity Guided Fractionation of the Rhizomes of *Cyperus rotundus* (FIG. 1

Methodology:
Dried rhizomes of *Cyperus rotundus* were pulverized to form a coarse powder. The pulverized powder was then extracted with 3 volumes of hexane followed by heating, reflux for 3 hours and filtering to obtain the hexane soluble fraction and spent material. The spent material is further extracted with 3 volumes of methanol followed by heating, reflux for 3 hours and filtering to obtain the methanol soluble active fraction and spent material. The methanol soluble fraction is solubilized in aqueous methanol and successively partitioned with chloroform (CHCl₃), Ethyl acetate (EtOAc) and methanol to obtain the chloroform layer, ethyl acetate layer and the aqueous methanol layer respectively. The chloroform layer, ethyl acetate layer and the aqueous methanol layer are subjected to further bioactivity guided fractionation, wherein the bioactivity parameter was the ability of the chloroform layer, ethyl acetate layer and the aqueous methanol layer to inhibit adipogenesis in 3T3-L1 mouse adipocytes (mammalian adipocytes). The steps of the Oil Red O staining technique as adapted from Salazar Olivo et al (1995), Wu Z et al (1998), Fu M et al (2005) to study extent of adipogenesis inhibition is explained in EXAMPLE 1A herein below. The results are mentioned in Table A.

Example 1A

Terminal differentiation of adipocytes is accompanied by the accumulation of great amounts of lipids in large cytoplasmic vesicles. A common assay to measure adipocyte differentiation in cell culture is with the dye Oil Red-O (ORO). ORO is a lipid-soluble bright red dye which is a reliable indicator of adipocyte differentiation.

Principle: Oil Red O (Solvent Red 27, Sudan Red 5B, C.I. 26125, and C26H24N4O) is a lysochrome (fat-soluble dye) diazo dye used for staining of neutral triglycerides and lipids on frozen sections and some lipoproteins on paraffin sections. It has the appearance of a red powder with maximum absorption at 518(359) nm. Oil Red O is one of the dyes used for Sudan staining. Similar dyes include Sudan III, Sudan IV, and Sudan Black B. The staining has to be performed on fresh samples, as alcohol fixation removes the lipids. Oil Red O largely replaced Sudan III and Sudan IV, as it provides much deeper red color and the stains are therefore much easier to see. Oil red 0 is an oil soluble dye. Oil soluble dyes exhibit greater solubility of the dye in lipoid substances in the tissues/cells, than in the usual hydro alcoholic dye solvents. Hence, it will deeply stain the cells.

3T3-L1 cells approximately 60×104 cells are seeded for 48-72 hrs to get 70-80% confluence. After 48 hrs 200 µl of AIM (Adipogenesis induction medium) freshly prepared is added. 72 hrs later 200 µl APM (Adipogenesis progression medium) with the test compounds in different concentrations is added to the wells. The cells are incubated for 48 hrs in a humidified atmosphere (370 C) of 5% CO2 and 95% air. The supernatant is collected and stored for the estimation of leptin, adiponectin, IL-6 and TNF-alpha. Cells are fixed by adding 100 µl of 10% formalin and ORO staining is done. OD is read at 492 nm in microplate reader.

The results are expressed as $IC_{50}$ values using Graphpad prism software. The percentage of inhibition of adipogenesis is calculated as follows, % Inhibition=C–T/T*100

Where C-absorbance of Oil red O in differentiating/undifferentiated cells
T-absorbance of Oil red O in sample treated differentiating/undifferentiated cells.

TABLE A

| Sample | Percent inhibition at variable concentration | | | | | $IC_{50}$ µg/ml |
|---|---|---|---|---|---|---|
| | 3.12 µg/ml | 6.25 µg/ml | 12.5 µg/ml | 25 µg/ml | 50 µg/ml | |
| Hexane layer | 1.29% | 12.09% | 18.97% | 26.25% | 40.13% | 52.22 |
| Methanol layer | -NIL- | 5.58% | 13.7% | 25.75% | 41.74% | 66.42 |
| CHCl3 layer | -NIL- | 8.91% | 9.58% | 24.21% | 26.66% | — |
| (EtOAc) layer | 18.98% | 26.77% | 53.55% | 73.63% | 88.41% | 9.39 |

The ethyl acetate layer exemplified the best bioactivity in terms of adipogenesis inhibition with an $IC_{50}$ (µg/ml) value of 9.39. This fraction was then subjected to column fractionation to identify the bioactivity (adipogenesis inhibition) biomarker. Column fractionation involved the step of eluting sub fractions of the ethyl acetate layer with increasing polarity of methanol: chloroform mixture. The sub fractions of ethyl acetate layer are labeled as I, II, III and IV are subjected to bioactivity (anti-adipogenesis) evaluation. The essential steps of anti-adipogenic activity evaluation involves the procedure outlined herein above EXAMPLE 1A. The results are summarized herein below in Table B.

TABLE B

| SAMPLE | $IC_{50}$ µg/ml |
|---|---|
| Sub fraction I (Non-polar constituents) | 23.21 |
| Sub fraction II (Naturally enriched in piceatannol along with dimers scirpusin A and scirpusin B) | 41.05 |
| Sub fraction III (Naturally enriched in piceatannol dimers scirpusin A and scirpusin B) | 13.31 |

TABLE B-continued

| SAMPLE | $IC_{50}$ µg/ml |
|---|---|
| Sub fraction IV (Naturally enriched in piceatannol dimers scirpusin A and scirpusin B) | 18.75 |

Figure 2:
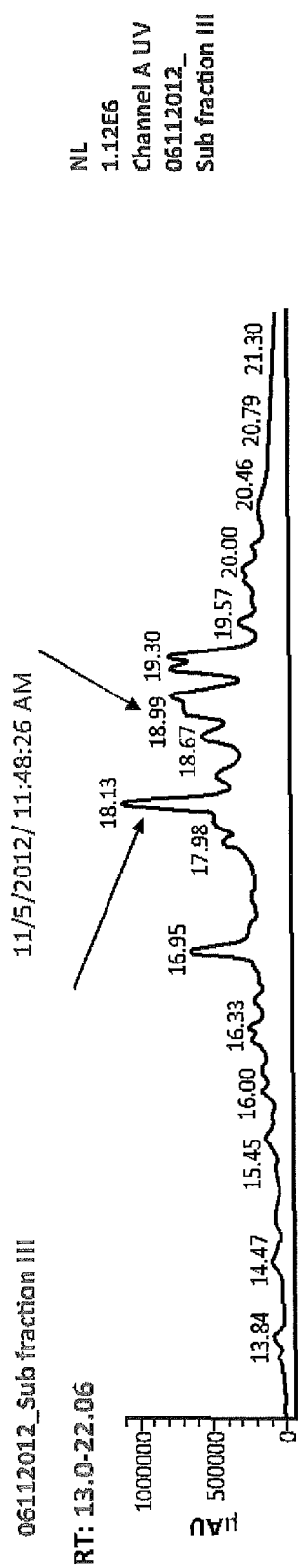
FIGS. 2, 2a, 2b and 3, 3a, 3b and 3c show the LC-MS analysis of subtractions III and IV respectively of the ethyl acetate layer naturally enriched with piceatannol dimers scirpusin A and scirpusin B.
Figure 2A:
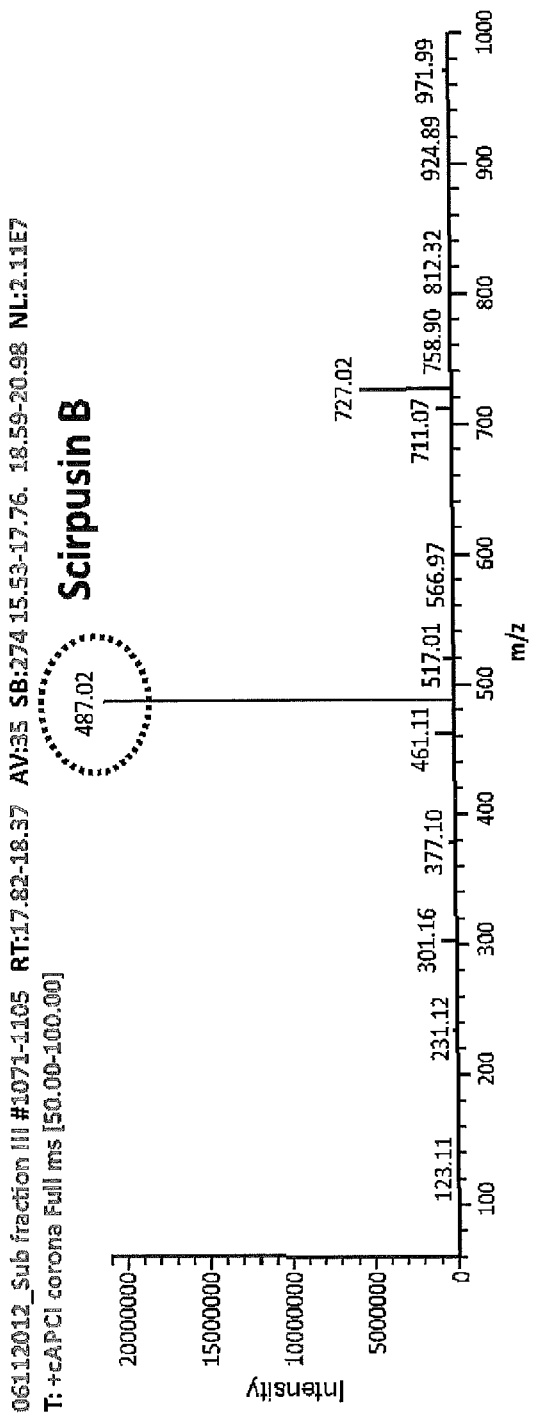
Figure 2B:
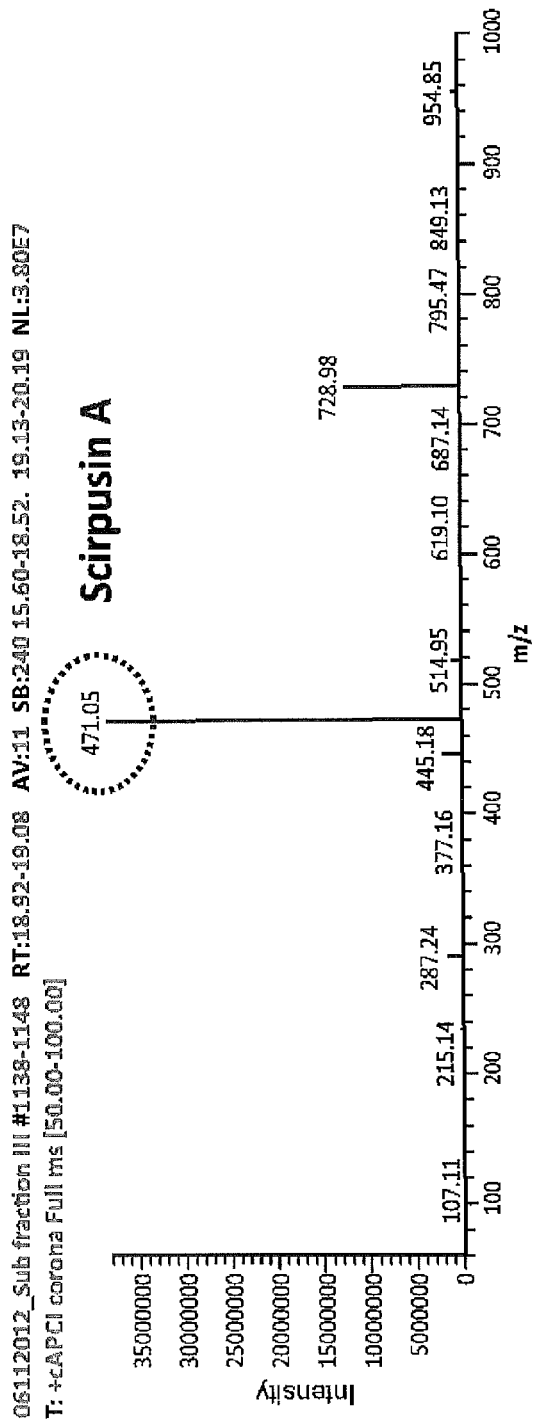
Figure 3:
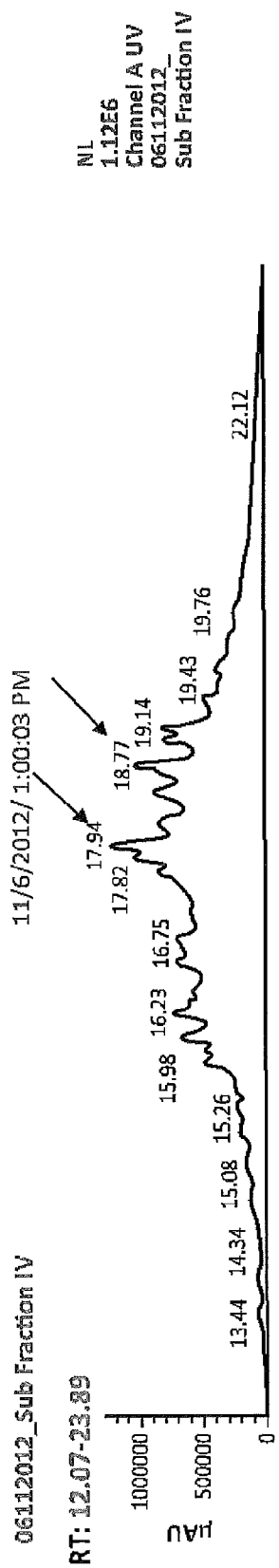
Figure 3A:
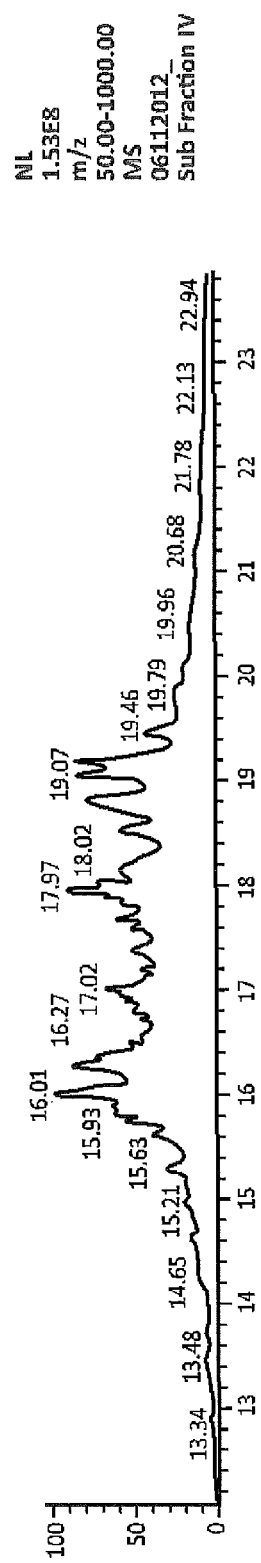
Figure 3B:
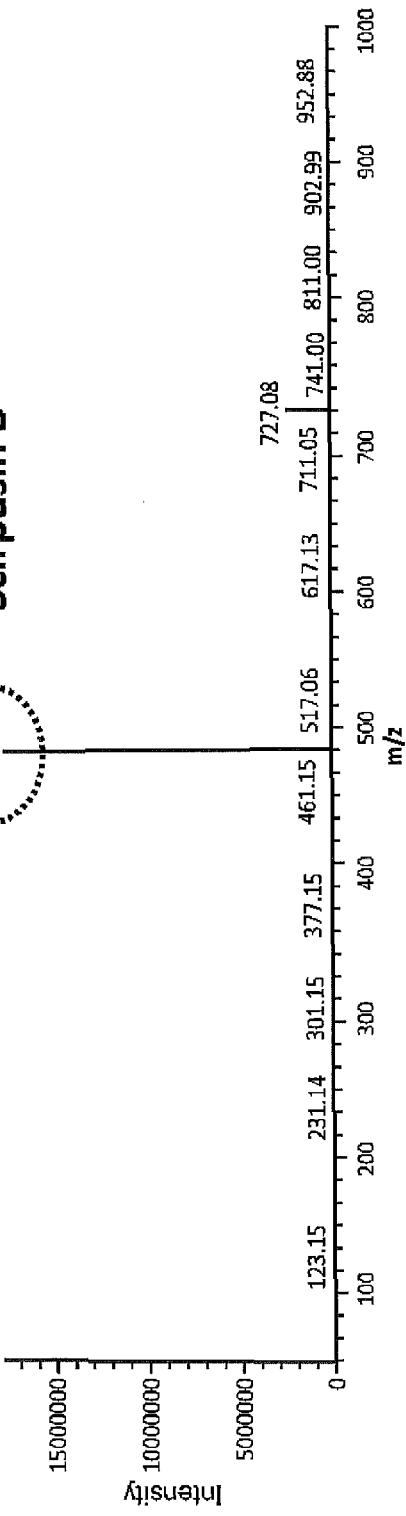
Figure 3C:
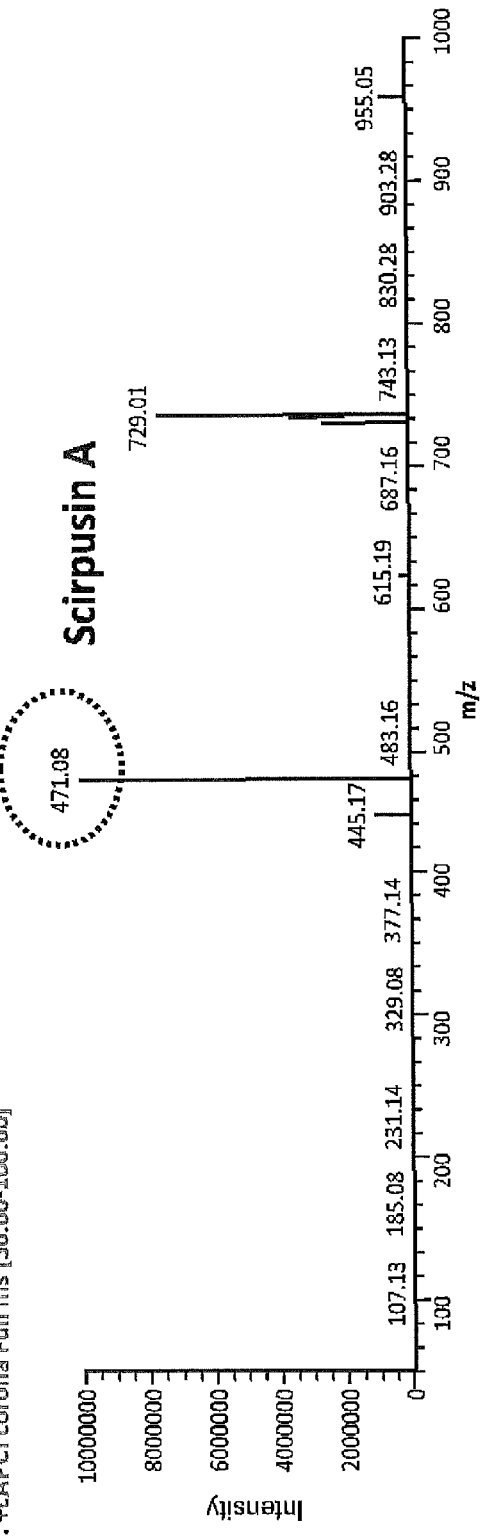

Sub fractions III and IV were then subjected to LC-MS with both fractions being enriched in piceatannol dimers scirpusin A and scirpusin B (FIGS. 2 and 3). The LC-MS/MS analysis was performed on Thermo Electronics Finnigan LCQ Advantage MAX spectrometer using an RP C18 column (250×4.6 mm, 5µ particle size). The system consisted of a Thermo-Finnigan surveyor PDA detector, an LC pump and an autosampler. The Mobile Phase included a Gradient run for 35 minutes with Solvent (A) 0.1% Acetic acid in water and Solvent (B) Acetonitrile. Solvent B concentration increased from 5% during 0-5 minutes, 5-60% during 5-20 minutes, 60-100% during 20-25 minutes, 100-5% during 25-27 minutes and remained constant at 5% during 27-35 minutes. The Stationary phase included Thermo BDS hypersil, C18 Column (Dimension—250 mm×4.6 mm); Flow rate: 1 ml/min; Detection Range: 260 nm Ionization parameters: APCI positive mode, Source voltage—4.50 kV, Capillary temperature—225 degrees, Capillary voltage—43.00 V.

Data interpretation: Mass of Scirpusin A is reported to be 470.13. The mass [M+H] observed at 18.77 min in positive ionization mode using the above protocol is 471.08. Mass of Scirpusin B is reported to be 486. The mass [M+H] observed at 17.94 min in positive ionization mode is 487.05.

The first level of confirmation of the presence of dimers of Piceatannol in the Cyperus extract was based on this preliminary information on mass. Scirpusin A was directly confirmed by direct comparison with an authentic sample of Scirpusin A.

Figure 4:
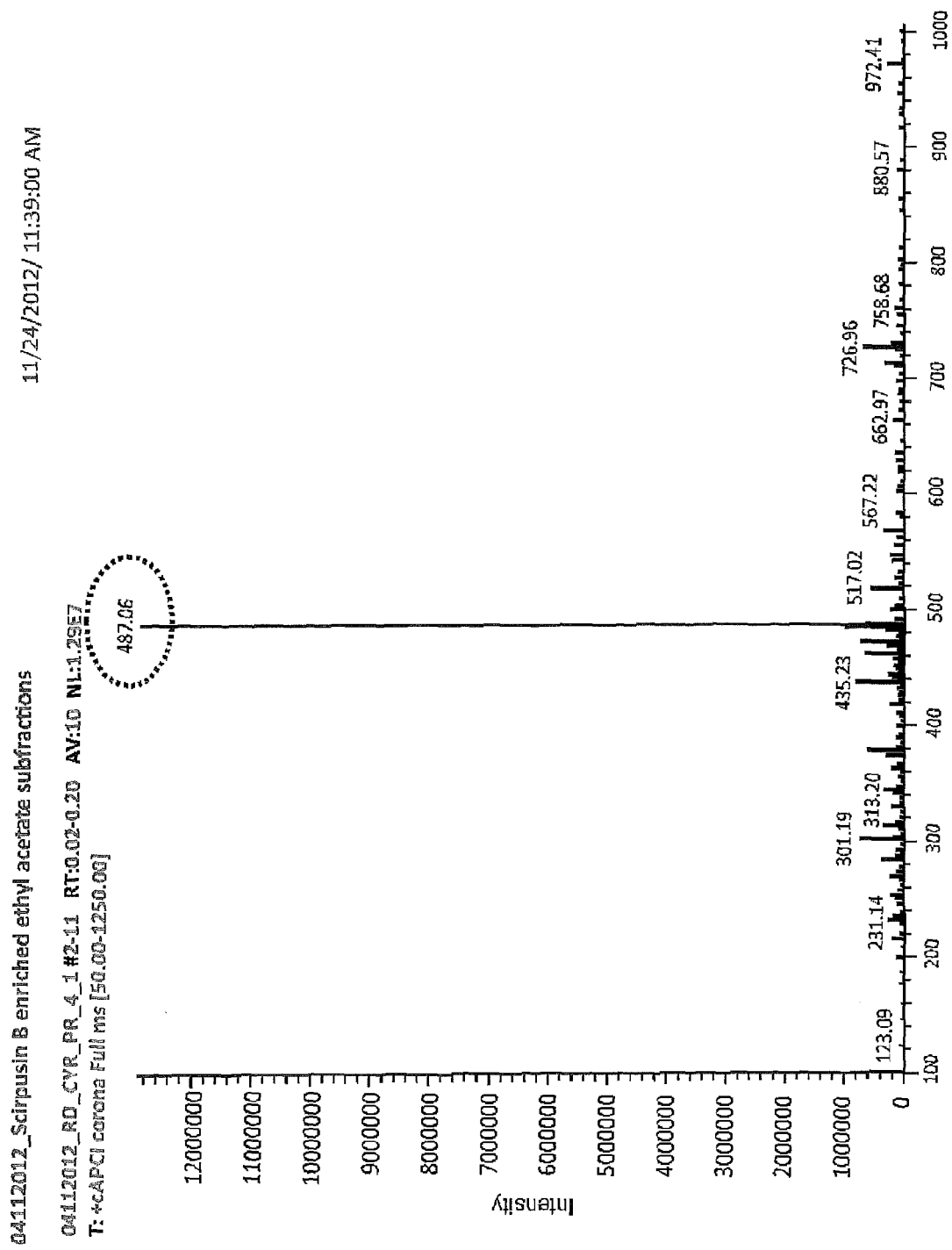
FIGS. 4 and 5 show the data from the HRMS indicating that the [M+H] values obtained therein correspond very well with the structure of the dimer and reported data (Sano et al., 2011) on the same.
Figure 5:
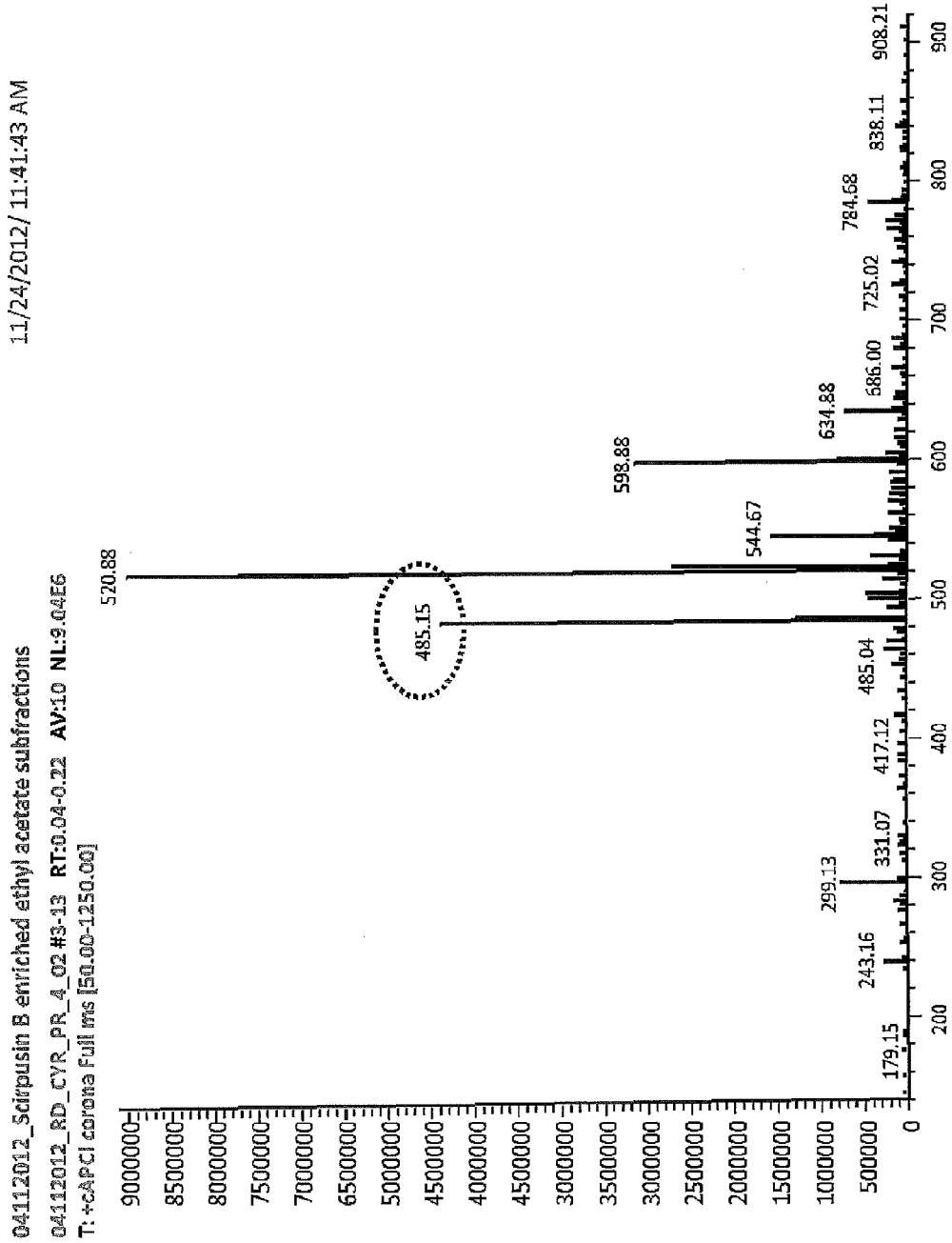

Subtractions were then subjected through the preparative HPLC to obtain purified dimer scirpusin B which was then studied using the analytical tools High Resolution Mass Spectroscopy (FIRMS), liquid chromatography-mass spectrometry (LC-MS/MS) and Nuclear Magnetic Resonance Spectroscopy (NMR) to be confirmed as scirpusin B. Data from the HRMS indicated [M+H]=487.138 which matched very well with the structure of the dimer and reported data (Sano et al., 2011) on the same (FIGS. 4 and 5) and the structure of scirpusin B was also confirmed using cryogenic probe NMR (FIG. 6). The compound was identified after comparison with the data available in literature (Sano et al., 2011). NMR data (CD3OD): δ: 56.73, 93.50, 95.39, 100.79, 102.93, 105.87×2, 112.21, 112.63, 114.83, 114.91, 117.03, 118.42, 118.61, 122.17, 129.46, 129.53, 133.53, 135.60, 144.90, 145.01, 145.09, 145.21, 146.27, 158.36, 158.56×2, 161.46. The APT (Attached Proton Test) NMR spectrum obtained at 500 MHz further confirmed the structure of Scirpusin B. Authentic sample of Scirpusin B was also isolated from passion fruits isolated by Sano et al., 2011 and compared directly with Scirpusin B isolated by us from *Cyperus rotundus* as described above and the identity of HPLC retention times, mass spec data and NMR data corroborated the presence of Scirpusin B in *Cyperus rotundus* in the most convincing way.

Example 2

Efficacy Evaluation for Anti-Obesity Effect of a Cypro-AD (Active Ethyl Acetate Fraction) AND CYPRO-D1 (Ethyl Acetate Subfraction Naturally Enriched in Piceatannol Dimers Scirpusin A and Scirpusin B) Extracts in Mice Objective of the test: The objective of the study was to evaluate the efficacy of Cypro-AF and Cypro-D1 extracts for anti-obesity effect in C57 mice.

Test System Details:

| | |
|---|---|
| Animal species | Mice |
| Strain | C57 |
| Body weight range | Males: 22-27 g; Females: 20-24 g |
| Age at treatment | 8-10 weeks |
| Number of Groups | 6 groups (One Control, One High fat diet control and Four treatment groups) |
| Number of animals/group | Each group contained 10 animals (5 Males + 5 Females). Female animals used were nulliparous and non-pregnant |
| Total No. of animals | 60 |
| Identification | Cage cards and individual animal ear notching method. |

Test Performance Details
Husbandry

| | |
|---|---|
| Conditions | The animals were housed under standard laboratory conditions, air-conditioned with adequate fresh air supply (Air changes 12-15 per hour), room temperature 22 ± 3 oC, relative humidity 30-70%, with 12 hours light and 12 hours dark cycle. The temperature and relative humidity were recorded once daily. |
| Housing | Individual animals were housed in a standard polypropylene cage (Size: L 290 × B 140 × H 140 mm) with stainless steel mesh top grill having facilities for holding pellet feed and drinking water in water bottle fitted with stainless steel sipper tube. Clean sterilized paddy husk was provided as bedding material. |
| Acclimatization | The animals were acclimatized for 7 days to laboratory conditions and were observed for clinical signs daily. |
| Diet | The animals were fed ad libitum with VRK's "Scientist's Choice" brand Laboratory animal feed manufactured by VRK Nutritional Solutions, Bibwewadi-Kondhwa Road, Pune. throughout the acclimatization period. D12450B diet (with 10 kcal % Fat) and D12492 High fat diet (with 60 kcal % Fat) manufactured by Research Diet Inc, USA procured from Indus Marketing, Hyderabad, Andhra Pradesh, INDIA was used for Induction of obesity and Main study. |
| Water | Clean drinking water was provided ad libitum throughout the acclimatization and Obesity induction period. Deep bore-well water passed through Reverse osmosis unit was provided in plastic water bottles with stainless steel sipper tubes. |

Grouping: Grouping of animals was done on the last day of acclimatization by body weight randomization and stratification method. Grouping of animals was done such that body weight variation of animals used does not exceed ±20% of the mean body weight of each group.

Study Design: The animals were divided into 6 groups viz., Group 1, 2, 3, 4, 5 and 6 consisting of 10 animals (5 male and 5 female) each. The group details, doses and number/sex of animals per group are presented in the following table:

| Group | Treatment | Dose (mg/kg Bwt) | Number of Animals Male | Number of Animals Female | Animal Numbers Male | Animal Numbers Female |
|---|---|---|---|---|---|---|
| G1 | Control (with 10 kcal % Fat) | — | 5 | 5 | 1-5 | 31-35 |
| G2 | High fat diet Control (with 60 kcal % Fat) | — | 5 | 5 | 6-10 | 36-40 |
| G3 | CYPRO-AF 50 mg/kg + High fat diet (with 60 kcal % Fat) | 50 | 5 | 5 | 11-15 | 41-45 |
| G4 | CYPRO-AF 100 mg/kg + High fat diet (with 60 kcal % Fat) | 100 | 5 | 5 | 16-20 | 46-50 |
| G5 | CYPRO-AF 200 mg/kg + High fat diet (with 60 kcal % Fat) | 200 | 5 | 5 | 21-25 | 51-55 |
| G6 | CYPRO-D1 - 10 mg/kg + High fat diet (with 60 kcal % Fat) | 10 | 5 | 5 | 26-30 | 56-60 |
| Total: | | | 30 | 30 | — | — |
| Total number of animals: | | | | 60 | | |

Formulation Details and Dosage

The test items Cypro-AF and Cypro-D1 were dissolved in distilled water for formulating different doses. Freshly formulated test items were administered through oral route by gavage. The volume of dosage per animal was maintained at 10 ml/kg body weight for all the animals throughout the study period. The following table provided details of the test formulation.

| Group | Dose (mg/kg Bwt) | Concentration (mg/ml) | Quantity (mg) | Volume of distilled water (ml) |
|---|---|---|---|---|
| G1 | — | — | — | 4.0 |
| G2 | — | — | — | 4.0 |
| G3 | 50 | 5 | 20 | 4.0 |
| G4 | 100 | 10 | 40 | 4.0 |
| G5 | 200 | 20 | 80 | 4.0 |
| G6 | 10 | 1 | 4 | 4.0 |

Obesity induction: The G1 Control group animals were fed with normal control diet feed D12450B containing 10 kcal % fat and the G2 to G6 group animals were fed with high fat diet feed D12492 containing 60 kcal % fat during the induction of obesity and during main study.

Main Study:

Main study was started after the induction of obesity. The 3 doses of Cypro-AF and 1 dose of Cypro-D1 were administered to animals from Day 28 daily consecutively for a period of 27 days. The feeding of the diets continued in the main study was done in induction of obesity. The G1 Control and G2 High fat diet control group animals administered with distilled water while other groups animals received test items from Day 28 to Day 54 of the study period. The dose volume of administration was maintained according to the weekly body weight of individual animals. The total duration of the study was 61 days (7 days Acclimatization period+27 days Induction of obesity+27 days Main study).

Observations

The following observations were made for during the study period.

Feed Consumption

Individual animal feed consumption were recorded. Weekly average feed consumption was calculated and recorded.

Body Weight

Individual animal body weights were recorded on the day of receipt on Day 1 and weekly (±1 day) thereafter during the study period.

Clinical Observations

All the animals were clinically observed twice daily during the study period.

Clinical Pathology

At the completion of the study period, blood samples were collected from the animals in tubes containing potassium ethylene di-amide tetra acetic acid (K2-EDTA) anticoagulant for hematology and without anticoagulant for clinical chemistry. The blood samples collected in tubes without anticoagulant were centrifuged at 3000 rpm for 10 minutes to obtain serum. Blood samples were collected humanely from retro-orbital plexus puncture method under mild ether anesthesia with the help of a fine capillary tube. The following hematology and clinical chemistry parameters were analyzed.

Hematology

The following hematology parameters were estimated using Sysmex, KX-21 (Transasia Bio-Medicals Ltd., India):

| Parameters | Units |
|---|---|
| Hemoglobin (Hb) | g/dL |
| Haematocrit (Hct) | % |
| Erythrocyte Count | $10^6$ cells/µL |
| Total Leukocyte Count | $10^3$ cells/µL |
| Mean corpuscular volume (MCV) | fL |
| Mean corpuscular hemoglobin (MCH) | Pg |
| Mean corpuscular hemoglobin concentration (MCHC) | g/dL |
| Platelet Count | $10^3$ cells/µL |
| Differential Leucocytes Count (DLC) | % |
| Clotting time | secs |

Clinical Chemistry

The following clinical chemistry parameters were analyzed using the "Erba Mannheim Chem Touch analyzer" (Transasia Bio-Medicals Ltd., India) from serum samples.

| Parameters | Units |
|---|---|
| Total Protein | g/dL |
| Albumin | g/dL |
| Glucose | mg/dL |
| Alanine aminotransferase (ALT) | IU/L |
| Aspartate aminotransferase (AST) | IU/L |
| Triglycerides | mg/dL |
| Total Cholesterol | mg/dL |
| High Density lipid (HDL) | mg/dL |
| Very Low density lipid (VLDL) | mg/dL |
| Low density Lipid (LDL) | mg/dL |

Pathology

After the completion of the study period, on Day 55, all the animals were humanely sacrificed by exposing them to excess carbon-di-oxide in gas chamber and subjected to following external and internal gross necropsy.

Gross Necropsy

The animals were subjected to external and internal gross pathological examinations.

Organ Weights

The following organs from all animals was trimmed of any adherent tissue, as appropriate and weighed wet as soon as possible to avoid drying: Brain, Thymus, Liver, Adrenals, Kidneys (paired organs), spleen, Heart, Ovaries/Testes (paired organs).

Fat Deposits Weights

The following fat deposits from all the animals was collected and weighed.
1. Epididymal Fat
2. Brown Fat
3. Ovarian Fat Statistical Analysis and Report Preparation The raw data obtained from the present study were subjected to computer statistical processing. The computer printout of the data (in the form of appendix) was verified with the original raw data. After verification, the data was subjected to One-way ANOVA (Analysis of Variance) with Dunnett's post test for the data on body weights, hematology and clinical chemistry parameters, organ weights using GraphPad Prism version 5.01, GraphPad Software. All analyses and comparisons will be evaluated at the 95% level of confidence (P<0.05), indicated by the designated by the superscripts of a where G1 is compared to G3, G4, G5, and G6 and b where G2 is compared to G3, G4, G5, and G6 throughout the report as stated below: *: Statistically significant (P<0.05) wherever applicable.

The data were subjected to One way—ANOVA statistical analysis by comparing the following:

G1 group {Control group (with 10 kcal % Fat)} to G3 group {CYPRO-AF 50 mg/kg+High fat diet (with 60 kcal % Fat)}, G4 group {CYPRO-AF −100 mg/kg+High fat diet (with 60 kcal % Fat)}, G5 group {CYPRO-AF 200 mg/kg+High fat diet (with 60 kcal % Fat)} and G6 group {CYPRO-D1 10 mg/kg+High fat diet (with 60 kcal % Fat)} as represented below:

| G1 group | G3 group |
|---|---|
| Control group | CYPRO-AF 50 mg/kg + |
| (with 10 kcal % Fat) | High fat diet (with 60 kcal % Fat) |
| | G4 group |
| | CYPRO-AF −100 mg/kg + High fat diet (with 60 kcal % Fat |
| | G5 group |
| | CYPRO-AF 200 mg/kg + High fat diet (with 60 kcal % Fat) |
| | G6 group |
| | CYPRO-D1 10 mg/kg + High fat diet (with 60 kcal % Fat) |

G2—High fat diet Control (with 60 kcal % Fat) to G3 group {CYPRO-AF 50 mg/kg+High fat diet (with 60 kcal % Fat)}, G4 group {CYPRO-AF −100 mg/kg+High fat diet (with 60 kcal % Fat)}, G5 group {CYPRO-AF 200 mg/kg+High fat diet (with 60 kcal % Fat)} and G6 group {CYPRO-D1 10 mg/kg+High fat diet (with 60 kcal % Fat)} as represented shown below:

| G2 group | G3 group |
|---|---|
| High fat diet Control | CYPRO-AF 50 mg/kg + |
| (with 60 kcal % Fat) | High fat diet (with 60 kcal % Fat) |
| | G4 group |
| | CYPRO-AF −100 mg/kg + High fat diet (with 60 kcal % Fat) |
| | G5 group |
| | CYPRO-AF 200 mg/kg + High fat diet (with 60 kcal % Fat) |
| | G6 group |
| | CYPRO-D1 10 mg/kg + High fat diet (with 60 kcal % Fat) |

Results

Feed Consumption

The summary of weekly average feed consumption of male and female animals is presented in Table-1 and Table-2 respectively. There were no statistical significant differences in the feed consumption of animals during the study period.

TABLE 1

Summary of weekly average feed consumption (g) of male animals
FEED CONSUMPTION (g)

| Group | Treatment | Days | | | | | | | |
|---|---|---|---|---|---|---|---|---|---|
| | | 7 | 14 | 21 | 28 | 35 | 42 | 49 | 54 |
| G1[a] | Control (with 10 kcal % fat) | 2.80 ± 0.13 | 3.50 ± 0.11 | 4.46 ± 0.10 | 4.55 ± 0.11 | 5.15 ± 0.18 | 4.63 ± 0.23 | 4.82 ± 0.19 | 5.10 ± 0.25 |
| G2[b] | High fat diet Control (with 60 kcal % Fat) | 2.86 ± 0.21 | 3.63 ± 0.15 | 4.38 ± 0.42 | 4.77 ± 0.21 | 5.00 ± 0.27 | 4.89 ± 0.20 | 4.83 ± 0.23 | 4.96 ± 0.14 |
| G3 | CYPRO-AF 50 mg/kg + High fat diet (with 60 kcal % Fat) | 2.79 ± 0.19 | 3.67 ± 0.14 | 4.45 ± 0.10 | 4.75 ± 0.19 | 5.12 ± 0.16 | 4.89 ± 0.35 | 4.96 ± 0.04 | 4.92 ± 0.47 |
| G4 | CYPRO-AF 100 mg/kg + High fat diet (with 60 kcal % Fat) | 2.73 ± 0.16 | 3.64 ± 0.19 | 4.27 ± 0.24 | 4.75 ± 0.18 | 5.12 ± 0.05 | 4.73 ± 0.28 | 4.99 ± 0.16 | 5.15 ± 0.19 |
| G5 | CYPRO-AF 200 mg/kg + High fat diet (with 60 kcal % Fat) | 2.99 ± 0.09 | 3.63 ± 0.15 | 4.41 ± 0.10 | 4.84 ± 0.06 | 5.20 ± 0.13 | 4.89 ± 0.14 | 5.02 ± 0.09 | 5.12 ± 0.12 |
| G6 | CYPRO-D1 10 mg/kg + High fat diet (with 60 kcal % Fat) | 2.87 ± 0.21 | 3.66 ± 0.18 | 4.34 ± 0.26 | 4.63 ± 0.25 | 5.03 ± 0.26 | 4.91 ± 0.10 | 5.01 ± 0.19 | 5.21 ± 0.25 | n = 5;
Values are Mean ± Standard Deviation;
P > 0.05

TABLE 2

Summary of weekly average feed consumption (G) of female animals
FEED CONSUMPTION

| Group | Treatment | Days | | | | | | | |
|---|---|---|---|---|---|---|---|---|---|
| | | 7 | 14 | 21 | 28 | 35 | 42 | 49 | 56 |
| G1[a] | Control (with 10 kcal % fat) | 2.90 ± 0.25 | 3.42 ± 0.30 | 3.87 ± 0.31 | 4.40 ± 0.51 | 4.88 ± 0.24 | 4.95 ± 0.15 | 4.54 ± 0.19 | 4.51 ± 0.15 |
| G2[b] | High fat diet Control (with 60 kcal % Fat) | 2.92 ± 0.37 | 3.53 ± 0.25 | 3.54 ± 0.33 | 4.17 ± 0.41 | 4.80 ± 0.36 | 4.59 ± 0.31 | 4.36 ± 0.08 | 4.43 ± 0.13 |
| G3 | CYPRO-AF 50 mg/kg + High fat diet (with 60 kcal % Fat) | 2.77 ± 0.26 | 3.27 ± 0.32 | 3.48 ± 0.22 | 4.27 ± 0.49 | 4.75 ± 0.55 | 5.11 ± 0.09 | 4.42 ± 0.14 | 4.33 ± 0.23 |
| G4 | CYPRO-AF 100 mg/kg + High fat diet (with 60 kcal % Fat) | 2.72 ± 0.15 | 3.40 ± 0.69 | 3.59 ± 0.37 | 4.59 ± 0.27 | 4.55 ± 0.33 | 4.89 ± 0.08 | 4.35 ± 0.21 | 4.38 ± 0.17 |
| G5 | CYPRO-AF 200 mg/kg + High fat diet (with 60 kcal % Fat) | 2.90 ± 0.38 | 3.34 ± 0.30 | 3.56 ± 0.46 | 4.37 ± 0.31 | 4.42 ± 0.39 | 5.02 ± 0.26 | 4.63 ± 0.30 | 4.26 ± 0.12 |

TABLE 2-continued

Summary of weekly average feed consumption (G) of female animals
FEED CONSUMPTION

| Group | Treatment | Days | | | | | | | |
|---|---|---|---|---|---|---|---|---|---|
| | | 7 | 14 | 21 | 28 | 35 | 42 | 49 | 56 |
| G6 | CYPRO-D1 10 mg/kg + High fat diet (with 60 kcal % Fat) | 3.08 ± 0.21 | 3.80 ± 0.53 | 3.59 ± 0.31 | 4.65 ± 0.28 | 4.54 ± 0.14 | 5.09 ± 0.19 | 4.56 ± 0.15 | 4.31 ± 0.19 | n = 5;
Values are Mean ± Standard Deviation;
P > 0.05

Body Weight

The summary of weekly body weight of male and female animals is presented in Table-3 and Table-4 respectively.

TABLE 3

Summary of body weight (G) of male animals
BODY WEIGHT (g)

| Group | Treatment | Days | | | | |
|---|---|---|---|---|---|---|
| | | 1 | 7 | 14 | 21 | 28 |
| G1[a] | Control (with 10 kcal % fat) | 23.34 ± 1.11 | 23.50 ± 0.93 | 23.88 ± 1.08 | 23.48 ± 0.86 | 25.04 ± 1.05 |
| G2[b] | High fat diet Control (with 60 kcal % Fat) | 23.48 ± 1.06 | 24.10 ± 0.86 | 24.58 ± 1.09 | 26.12 ± 1.12 | 28.48 ± 1.98 |
| G3 | CYPRO-AF 50 mg/kg + High fat diet (with 60 kcal % Fat) | 23.42 ± 1.06 | 24.30 ± 1.63 | 24.90 ± 1.71 | 25.96 ± 1.49 | 27.80 ± 2.84 |
| G4 | CYPRO-AF 100 mg/kg + High fat diet (with 60 kcal % Fat) | 23.24 ± 1.18 | 23.78 ± 1.62 | 24.68 ± 1.48 | 26.14 ± 2.12 | 28.70 ± 1.72 |
| G5 | CYPRO-AF 200 mg/kg + High fat diet (with 60 kcal % Fat) | 23.60 ± 1.03 | 24.32 ± 0.60 | 24.98 ± 1.31 | 26.08 ± 1.01 | 28.90 ± 0.82 |
| G6 | CYPRO-D1 10 mg/kg + High fat diet (with 60 kcal % Fat) | 23.68 ± 1.20 | 24.50 ± 1.19 | 25.24 ± 1.18 | 26.26 ± 1.53 | 29.04 ± 3.11 |

| Group | Days | | | |
|---|---|---|---|---|
| | 35 | 42 | 49 | 55 |
| G1[a] | 26.70 ± 1.40 | 28.62 ± 3.31 | 29.16 ± 3.75 | 31.00 ± 4.12 |
| G2[b] | 30.72 ± 1.72 | 32.50 ± 1.53 | 33.66 ± 1.78 | 35.20 ± 0.95 |
| G3 | 29.48 ± 3.50 | 30.28 ± 3.39 | 30.98 ± 2.95 | 33.34 ± 1.78 |
| G4 | 29.22 ± 3.06 | 30.04 ± 3.38 | 30.00 ± 2.85 | 32.94 ± 2.49 |
| G5 | 30.60 ± 1.65 | 30.50 ± 3.28 | 31.06 ± 3.61 | 33.46 ± 3.40 |
| G6 | 29.62 ± 3.76 | 29.86 ± 2.86 | 30.58 ± 2.63 | 33.38 ± 2.76 | n = 5;
Values are Mean ± Standard Deviation;
P > 0.05

TABLE 4

Summary of body weight (G) of female animals
BODY WEIGHT (g)

| | | Days | | | | |
|---|---|---|---|---|---|---|
| Group | Treatment | 1 | 7 | 14 | 21 | 28 |
| G1[a] | Control (with 10 kcal % fat) | 21.08 ± 0.82 | 21.70 ± 0.81 | 22.24 ± 0.26 | 23.12 ± 0.68 | 23.98 ± 1.17 |
| G2[b] | High fat diet Control (with 60 kcal % Fat) | 21.38 ± 1.02 | 22.02 ± 0.67 | 22.20 ± 0.98 | 23.10 ± 0.76 | 25.04 ± 0.34 |
| G3 | CYPRO-AF 50 mg/kg + High fat diet (with 60 kcal % Fat) | 21.14 ± 0.87 | 21.76 ± 0.36 | 22.76 ± 0.68 | 24.30 ± 0.85 | 25.84 ± 0.81 |
| G4 | CYPRO-AF 100 mg/kg + High fat diet (with 60 kcal % Fat) | 21.32 ± 1.03 | 21.62 ± 1.53 | 23.68 ± 1.08 | 25.56 ± 1.19 | 26.32 ± 0.69 |
| G5 | CYPRO-AF 200 mg/kg + High fat diet (with 60 kcal % Fat) | 20.94 ± 0.95 | 21.32 ± 1.18 | 23.14 ± 0.97 | 24.94 ± 1.32 | 26.12 ± 0.98 |
| G6 | CYPRO-D1 10 mg/kg + High fat diet (with 60 kcal % Fat) | 21.34 ± 1.27 | 21.58 ± 0.69 | 23.16 ± 1.08 | 25.46 ± 0.86 | 26.72 ± 0.61 |

| | Days | | | |
|---|---|---|---|---|
| Group | 35 | 42 | 49 | 55 |
| G1[a] | 24.82 ± 2.41 | 25.10 ± 2.59 | 26.12 ± 1.91 | 27.74 ± 1.02 |
| G2[b] | 26.40 ± 0.89 | 28.26 ± 0.78 | 30.70 ± 1.70 | 33.02 ± 1.80 |
| G3 | 25.30 ± 1.35 | 26.62 ± 1.68 | 28.66 ± 1.01 | 30.58 ± 1.76 |
| G4 | 26.30 ± 1.30 | 26.84 ± 2.34 | 28.08 ± 3.07 | 30.30 ± 3.54 |
| G5 | 25.90 ± 1.23 | 26.30 ± 2.04 | 27.62 ± 1.06 | 30.22 ± 1.63 |
| G6 | 26.18 ± 0.98 | 26.08 ± 1.47 | 28.44 ± 1.82 | 29.78 ± 1.74 | n = 5;
Values are Mean ± Standard Deviation;
*Significant difference, P < 0.05

In male animals, there was statistical significant increase in mean weekly body weight values of on Day 21 in G3 group {CYPRO-AF –50 mg/kg+High fat diet (with 60 kcal % Fat)}, G4 group {CYPRO-AF –100 mg/kg+High fat diet (with 60 kcal % Fat)}, G5 group {CYPRO-AF –200 mg/kg+High fat diet (with 60 kcal % Fat)} and G6 group {CYPRO-D1 –10 mg/kg+High fat diet (with 60 kcal % Fat)} compared to G1 group {Control group (with 10 kcal % Fat)}. These changes were considered to be due to difference in fat content of the feed.

In male animals, there was statistical significant increase in mean weekly body weight values of on Day 28 in G4 group {CYPRO-AF –100 mg/kg+High fat diet (with 60 kcal % Fat)}, G5 group {CYPRO-AF –200 mg/kg+High fat diet (with 60 kcal % Fat)} and G6 group {CYPRO-D1 –10 mg/kg+High fat diet (with 60 kcal % Fat)} compared to G1 group {Control group (with 10 kcal % Fat)}. These changes were considered to be due to difference in fat content of the feed.

In male animals, there was decrease in mean weekly body weight values of on Day 35, 42, 49 and 55 in G3 group {CYPRO-AF –50 mg/kg+High fat diet (with 60 kcal % Fat)}, G4 group {CYPRO-AF –100 mg/kg+High fat diet (with 60 kcal % Fat)}, G5 group {CYPRO-AF –200 mg/kg+High fat diet (with 60 kcal % Fat)} and G6 group {CYPRO-D1 –10 mg/kg+High fat diet (with 60 kcal % Fat)} compared to G1 group {Control group (with 10 kcal % Fat)}. These changes were considered to be due to administration of test items.

In female animals, there was statistical significant increase in mean weekly body weight values of on Day 21 in G4 group {CYPRO-AF –100 mg/kg+High fat diet (with 60 kcal % Fat)}, G5 group {CYPRO-AF –200 mg/kg+High fat diet (with 60 kcal % Fat)} and G6 group {CYPRO-D1 –10 mg/kg+High fat diet (with 60 kcal % Fat)} compared to G1 group {Control group (with 10 kcal % Fat)}. These changes were considered to be due to difference in fat content of the feed.

In female animals, there was statistical significant increase in mean weekly body weight values of on Day 28 in G3 group {CYPRO-AF –50 mg/kg+High fat diet (with 60 kcal % Fat)}, G4 group {CYPRO-AF –100 mg/kg+High fat diet (with 60 kcal % Fat)}, G5 group {CYPRO-AF –200 mg/kg+High fat diet (with 60 kcal % Fat)} and G6 group {CYPRO-D1 –10 mg/kg+High fat diet (with 60 kcal % Fat)} compared to G1 group {Control group (with 10 kcal % Fat)}. These change were considered to be due to difference in fat content of the feed.

In female animals, there was decrease in mean weekly body weight values of on Day 35, 42, 49 and 55 in G3 group {CYPRO-AF –50 mg/kg+High fat diet (with 60 kcal % Fat)}, G4 group {CYPRO-AF –100 mg/kg+High fat diet (with 60 kcal % Fat)}, G5 group {CYPRO-AF –200 mg/kg+High fat diet (with 60 kcal % Fat)} and G6 group {CYPRO-D1 –10 mg/kg+High fat diet (with 60 kcal % Fat)} compared to G1 group {Control group (with 10 kcal % Fat)}. These change were considered to be due to administration of test items.

Clinical Observations

The summary of clinical signs of male and female animals is presented in Table-5 and Table-6 respectively. The animals were found to healthy and normal in health status during the clinical observations during the study period.

TABLE 5

Summary of Clinical Signs Observations in Male Animals
CLINICAL SIGNS OBSERVATIONS

| Group | Treatment | \multicolumn{9}{c}{Days} |
|---|---|---|---|---|---|---|---|---|---|---|
| | | 1 | 2-7 | 8-14 | 15-21 | 22-28 | 29-35 | 36-42 | 43-49 | 50-55 |
| G1[a] | Control (with 10 kcal % fat) | N | N | N | N | N | N | N | N | N |
| G2[b] | High fat diet Control (with 60 kcal % Fat) | N | N | N | N | N | N | N | N | N |
| G3 | CYPRO-AF 50 mg/kg + High fat diet (with 60 kcal % Fat) | N | N | N | N | N | N | N | N | N |
| G4 | CYPRO-AF 100 mg/kg + High fat diet (with 60 kcal % Fat) | N | N | N | N | N | N | N | N | N |
| G5 | CYPRO-AF 200 mg/kg + High fat diet (with 60 kcal % Fat) | N | N | N | N | N | N | N | N | N |
| G6 | CYPRO-D1 10 mg/kg + High fat diet (with 60 kcal % Fat) | N | N | N | N | N | N | N | N | N | n = 5;
N—Normal

TABLE 6

Summary of clinical signs observations of female animals
CLINICAL SIGNS OBSERVATIONS

| Group | Treatment | \multicolumn{9}{c}{Days} |
|---|---|---|---|---|---|---|---|---|---|---|
| | | 1 | 2-7 | 8-14 | 15-21 | 22-28 | 29-35 | 36-42 | 43-49 | 50-55 |
| G1[a] | Control (with 10 kcal % fat) | N | N | N | N | N | N | N | N | N |
| G2[b] | High fat diet Control (with 60 kcal % Fat) | N | N | N | N | N | N | N | N | N |
| G3 | CYPRO-AF 50 mg/kg + High fat diet (with 60 kcal % Fat) | N | N | N | N | N | N | N | N | N |
| G4 | CYPRO-AF 100 mg/kg + High fat diet (with 60 kcal % Fat) | N | N | N | N | N | N | N | N | N |
| G5 | CYPRO-AF 200 mg/kg + High fat diet (with 60 kcal % Fat) | N | N | N | N | N | N | N | N | N |

TABLE 6-continued

Summary of clinical signs observations of female animals
CLINICAL SIGNS OBSERVATIONS

| | | Days | | | | | | | | |
|---|---|---|---|---|---|---|---|---|---|---|
| Group | Treatment | 1 | 2-7 | 8-14 | 15-21 | 22-28 | 29-35 | 36-42 | 43-49 | 50-55 |
| G6 | CYPRO-D1 10 mg/kg + High fat diet (with 60 kcal % Fat) | N | N | N | N | N | N | N | N | N | n = 5;
N—Normal

Hematology

The summary of hematological parameters estimations of male and female animals is presented in Table-7 and Table-8 respectively.

TABLE 7

Summary of hematology of male animals

| Group | Treatment | TLC ($10^3$ cells/μL) | TEC ($10^6$ cells/μL) | Hb g/dL | Hct (%) | MCV (fL) | MCH (pg) |
|---|---|---|---|---|---|---|---|
| G1[a] | Control with 10 kcal % fat | 9.34 ± 1.88 | 9.19 ± 0.48 | 13.04 ± 0.71 | 46.18 ± 3.65 | 50.22 ± 1.63 | |
| G2[b] | High fate Control with 60 kcal % fat | 13.16 ± 7.95 | 9.25 ± 0.80 | 13.30 ± 0.82 | 46.44 ± 3.17 | 50.26 ± 0.86 | |
| G3 | CYPRO-AF 50 mg/kg + High fat diet | 7.34 ± 3.51 | 9.48 ± 0.75 | 13.74 ± 1.09 | 48.08 ± 4.30 | 50.72 ± 2.04 | |
| G4 | CYPRO-AF 100 mg/kg + High fat diet (with 60 kcal % Fat) | 10.08 ± 7.35 | 9.06 ± 1.19 | 13.34 ± 0.86 | 44.70 ± 5.39 | 49.40 ± 1.31 | |
| G5 | CYPRO-AF 200 mg/kg + High fat diet (with 60 kcal % Fat) | 7.44 ± 3.64 | 8.93 ± 1.11 | 13.00 ± 1.82 | 44.84 ± 6.55 | 50.04 ± 1.76 | |
| G6 | CYPRO-D1 10 mg/kg + High fat diet (with 60 kcal % Fat) | 9.30 ± 3.51 | 9.57 ± 0.77 | 13.74 ± 0.50 | 47.08 ± 2.16 | 49.32 ± 2.09 | |

| Group | MCH (g/dL) | MCHC (g/dL) | Platelet Count ($10^3$ cells/μL) |
|---|---|---|---|
| G1[a] | 14.20 ± 0.40 | 28.28 ± 1.11 | 1167.20 ± 139.82 |
| G2[b] | 14.40 ± 0.74 | 28.68 ± 1.27 | 1297.80 ± 176.81 |
| G3 | 14.50 ± 0.46 | 28.58 ± 0.49 | 1297.00 ± 232.56 |
| G4 | 14.86 ± 1.22 | 30.04*[a] ± 1.95 | 1313.20 ± 159.37 |
| G5 | 14.52 ± 0.45 | 29.02 ± 0.33 | 1465.60 ± 168.11 |
| G6 | 14.42 ± 0.75 | 29.20 ± 0.62 | 1389.60 ± 278.21 |

HEMATOLOGY PARAMETERS

| | | Clotting | Differential Leucocyte Count | | | | |
|---|---|---|---|---|---|---|---|
| Group | Treatment | time (sec) | Neutrophils (%) | Lymphocytes (%) | Monocytes (%) | Eosinophils (%) | Basophils (%) |
| G1[a] | Control with 10 kcal % fat | 106.80 ± 10.47 | 21.40 ± 3.21 | 70.00 ± 1.58 | 6.40 ± 1.52 | 0.80 ± 0.45 | 1.60 ± 0.89 |

TABLE 7-continued

Summary of hematology of male animals

| | | | | | | | | |
|---|---|---|---|---|---|---|---|---|
| G2[b] | High fat Control with 60 kcal % fat | 110.80 ± 14.86 | 20.00 ± 3.94 | 73.00 ± 3.16 | 6.00 ± 1.58 | 0.60 ± 0.55 | 1.00 ± 0.71 | |
| G3 | CYPRO-AF 50 mg/kg + High fat diet | 111.20 ± 17.80 | 20.40 ± 2.30 | 71.00 ± 3.08 | 6.60 ± 1.14 | 0.80 ± 0.45 | 1.40 ± 0.89 | |
| G4 | CYPRO-AF 100 mg/kg + High fat diet (with 60 kcal % Fat) | 112.20 ± 13.46 | 19.80 ± 3.19 | 72.80 ± 3.42 | 5.80 ± 1.92 | 0.60 ± 0.55 | 1.40 ± 0.55 | |
| G5 | CYPRO-AF 200 mg/kg + High fat diet (with 60 kcal % Fat) | 101.00 ± 11.45 | 22.00 ± 2.00 | 68.80 ± 1.64 | 7.00 ± 1.00 | 0.80 ± 0.45 | 1.40 ± 0.55 | |
| G6 | CYPRO-D1 10 mg/kg + High fat diet (with 60 kcal % Fat) | 113.20 ± 13.10 | 21.40 ± 2.88 | 70.40 ± 4.16 | 5.80 ± 1.30 | 0.60 ± 0.55 | 1.80 ± 0.84 | | n = 5;
Values - Mean ± Standard Deviation;
P > 0.05

TABLE 8

Summary of hematology of female animals

| Group | Treatment | TLC ($10^3$ cells/μL) | TEC ($10^6$ cells/μL) | Hb g/dL | Hct (%) | MCV (fL) | MCV (pg) |
|---|---|---|---|---|---|---|---|
| G1[a] | Control with 10 kcal % fat | 8.74 ± 2.96 | 9.94 ± 0.70 | 13.84 ± 0.81 | 50.06 ± 3.81 | 50.36 ± 1.76 | |
| G2[b] | High fate Control with 60 kcal % fat | 8.16 ± 2.55 | 8.97 ± 1.13 | 13.16 ± 1.72 | 45.74 ± 6.65 | 50.88 ± 1.58 | |
| G3 | CYPRO-AF 50 mg/kg + High fat diet | 7.06 ± 1.87 | 9.47 ± 0.22 | 14.00 ± 0.50 | 49.84 ± 1.34 | 52.60*[a] ± 0.31 | |
| G4 | CYPRO-AF 100 mg/kg + High fat diet (with 60 kcal % Fat) | 10.56 ± 5.49 | 9.25 ± 0.49 | 13.48 ± 0.73 | 47.50 ± 3.24 | 51.32 ± 1.34 | |
| G5 | CYPRO-AF 200 mg/kg + High fat diet (with 60 kcal % Fat) | 7.82 ± 3.18 | 9.73 ± 0.70 | 13.34 ± 0.93 | 49.32 ± 2.70 | 50.74 ± 1.55 | |
| G6 | CYPRO-D1 10 mg/kg + High fat diet (with 60 kcal % Fat) | 7.40 ± 2.20 | 9.61 ± 0.52 | 13.82 ± 0.54 | 48.78 ± 1.91 | 50.82 ± 1.13 | |

| Group | MCH (g/dL) | MCHC (g/dL) | Platelet Count ($10^3$ cells/μL) |
|---|---|---|---|
| G1[a] | 13.94 ± 0.72 | 27.68 ± 1.00 | 1195.40 ± 273.99 |
| G2[b] | 14.66 ± 0.50 | 28.82 ± 0.77 | 1241.80 ± 245.80 |
| G3 | 14.76*[a] ± 0.29 | 28.10 ± 0.51 | 1144.00 ± 144.65 |
| G4 | 14.58 ± 0.44 | 28.40 ± 0.70 | 1124.00 ± 152.23 |
| G5 | 13.72**[b] ± 0.39 | 27.04**[b] ± 0.58 | 1109.60 ± 223.81 |
| G6 | 14.40 ± 0.42 | 28.36 ± 0.84 | 1111.60 ± 180.93 |

TABLE 8-continued

Summary of hematology of female animals

HEMATOLOGY PARAMETERS

| Group | Treatment | Clotting time (sec) | Differential Leucocyte Count | | | | |
|---|---|---|---|---|---|---|---|
| | | | Neutrophils (%) | Lymphocytes (%) | Monocyte (%) | Eosinophil (%) | Basophil (%) |
| G1[a] | Control with 10 kcal % fat | 105.60 ± 14.17 | 18.80 ± 3.90 | 74.60 ± 4.45 | 5.40 ± 0.89 | 0.80 ± 0.45 | 1.40 ± 0.89 |
| G2[b] | High fat Control with 60 kcal % fat | 108.60 ± 12.74 | 21.00 ± 3.00 | 72.00 ± 1.87 | 6.20 ± 1.79 | 0.40 ± 0.55 | 1.40 ± 0.55 |
| G3 | CYPRO-AF 50 mg/kg + High fat diet | 117.60 ± 14.79 | 19.60 ± 3.85 | 73.20 ± 4.15 | 5.20 ± 1.10 | 0.80 ± 0.84 | 1.20 ± 0.84 |
| G4 | CYPRO-AF 100 mg/kg + High fat diet (with 60 kcal % Fat) | 104.60 ± 12.05 | 20.40 ± 4.62 | 72.00 ± 4.80 | 6.00 ± 1.58 | 0.80 ± 0.45 | 1.20 ± 0.45 |
| G5 | CYPRO-AF 200 mg/kg + High fat diet (with 60 kcal % Fat) | 111.20 ± 14.25 | 21.60 ± 3.97 | 69.20 ± 3.96 | 7.00 ± 0.71 | 1.00 ± 0.71 | 1.00 ± 0.71 |
| G6 | CYPRO-D1 10 mg/kg + High fat diet (with 60 kcal % Fat) | 109.40 ± 12.54 | 20.60 ± 3.51 | 71.00 ± 2.65 | 6.20 ± 1.48 | 0.80 ± 0.84 | 1.00 ± 0.71 | n = 5;
Values - Mean ± Standard Deviation;
P > 0.05

Hematology parameters statistical analysis comparison between G1 to G3, G4, G5, and G6

Mean Corpuscular Hemoglobin Concentration (MCHC)

In male animals, there was statistical significant increase in mean MCHC value of G4 group {CYPRO-AF −100 mg/kg+ High fat diet (with 60 kcal % Fat)} compared to G1 group {Control group (with 10 kcal % Fat)}. These changes can be considered as incidental as there was no dose dependent response.

Mean Corpuscular Volume and Mean Corpuscular Hemoglobin

In female animals, there was statistical significant increase in mean MCV and MCH values of G3 group {CYPRO-AF −50 mg/kg+High fat diet (with 60 kcal % Fat)} compared to G1 group {Control group (with 10 kcal % Fat)}. These changes can be considered as incidental as there was no dose dependent response.

Mean Corpuscular Hemoglobin and Mean Corpuscular Hemoglobin Concentration

In female animals, there was statistical significant increase in mean MCH and MCHC values of G5 group {CYPRO-AF −200 mg/kg+High fat diet (with 60 kcal % Fat)} compared to G2 group {High fat diet control group (with 60 kcal % Fat)}. This change can be considered as incidental as there was no dose dependent response.

Clinical Chemistry

The summary of clinical chemistry parameters estimations of male and female animals is presented in Table-9 and Table-10 respectively.

TABLE 9

CLINICAL CHEMISTRY PARAMETERS IN MALE ANIMALS

| Group | Treatment | Total Protein (g/dl) | Albumin (g/dl) | Glucose (mg/dl) | ALT/SGPT (IU/L) | AST/SGOT (IU/L) | Triglyceride (mg/dl) | Total Cholesterol (mg/dl) |
|---|---|---|---|---|---|---|---|---|
| G1[a] | Control (with 10 kcal % Fat) | 6.39 ± 0.39 | 2.73 ± 0.44 | 102.96 ± 48.15 | 58.74 ± 15.21 | 108.69 ± 28.77 | 122.28 ± 36.20 | 86.99 ± 16.72 |
| G2[b] | High fat diet Control (with 60 kcal % Fat) | 7.14 ± 2.31 | 2.70 ± 0.20 | 106.86 ± 34.32 | 55.37 ± 35.47 | 98.57 ± 25.20 | 110.07 ± 19.34 | 128.94 ± 19.01 |
| G3 | CYPRO-AF 50 mg/kg + High fat diet (with 60 kcal % Fat) | 6.15 ± 0.26 | 2.71 ± 0.13 | 93.65 ± 28.95 | 59.42 ± 24.88 | 106.00 ± 23.46 | 94.93 ± 18.82 | 127.31*[a] ± 32.60 |

TABLE 9-continued

| | | | | | | | | |
|---|---|---|---|---|---|---|---|---|
| G4 | CYPRO-AF 100 mg/kg + High fat diet (with 60 kcal % Fat) | 6.20 ± 0.23 | 2.64 ± 0.23 | 120.34 ± 19.04 | 56.04 ± 25.33 | 84.41 ± 28.56 | 99.65 ± 18.16 | 123.79 ± 25.80 |
| G5 | CYPRO-AF 100 mg/kg + High fat diet (with 60 kcal % Fat) | 6.13 ± 0.61 | 2.57 ± 0.35 | 107.18 ± 37.36 | 42.54 ± 20.06 | 74.28 ± 22.79 | 95.36 ± 18.13 | 107.19 ± 19.26 |
| G6 | CYPRO-D1 10 mg/kg + High fat diet (with 60 kcal % Fat) | 6.50 ± 0.37 | 2.56 ± 0.35 | 103.20 ± 43.46 | 51.31 ± 23.80 | 71.58 ± 20.61 | 97.18 ± 21.58 | 130.72*[a] ± 15.34 |

CLINICAL CHEMISTRY PARAMETERS

| Group | Treatment | HDL (mg/dl) | VLDL (mg/dl) | LDL (mg/dl) |
|---|---|---|---|---|
| G1[a] | Control (with 10 kcal % Fat) | 45.12 ± 16.79 | 24.46 ± 7.24 | 45.46 ± 13.24 |
| G2[b] | High fat diet Control (with 60 kcal % Fat) | 85.48 ± 23.04 | 22.01 3.87 | 66.84 ± 17.14 |
| G3 | CYPRO-AF 50 mg/kg + High fat diet (with 60 kcal % Fat) | 40.04***[b] ± 7.49 | 18.99 ± 3.76 | 78.70**[a] ± 14.09 |
| G4 | CYPRO-AF 100 mg/kg + High fat diet (with 60 kcal % Fat) | 55.90**[b] ± 15.76 | 19.93 ± 3.63 | 75.16**[a] ± 17.74 |
| G5 | CYPRO-AF 200 mg/kg + High fat diet (with 60 kcal % Fat) | 20.09**[ab] ± 7.51 | 19.07 ± 3.63 | 59.99 ± 13.73 |
| G6 | CYPRO-D1 10 mg/kg + High fat diet (with 60 kcal % Fat) | 26.82*[b] ± 5.45 | 19.44 ± 4.32 | 81.31*[a] ± 11.64 | n = 5;
Values - Mean ± Standard Deviation;
$P < 0.05$

TABLE 10

CLINICAL CHEMISTRY PARAMETERS IN FEMALE ANIMALS

| Group | Treatment | Total Protein (g/dl) | Albumin (g/dl) | Glucose (mg/dl) | ALT/SGPT (IU/L) | AST/SGOT (IU/L) | Triglyceride (mg/dl) | Total Cholesterol (mg/dl) |
|---|---|---|---|---|---|---|---|---|
| G1[a] | Control (with 10 kcal % Fat) | 6.78 ± 0.36 | 3.11 ± 0.13 | 78.96 ± 18.98 | 40.51 ± 30.20 | 85.76 ± 39.56 | 97.65 ± 36.05 | 75.03 ± 11.41 |
| G2[b] | High fat diet Control (with 60 kcal % Fat) | 6.70 ± 0.72 | 2.86 ± 0.36 | 89.91 ± 26.14 | 35.11 ± 9.73 | 71.58 ± 21.82 | 69.94 ± 35.70 | 97.70 ± 10.92 |
| G3 | CYPRO-AF 50 mg/kg + High fat diet (with 60 kcal % Fat) | 6.23*[a] ± 0.22 | 2.99 ± 0.24 | 85.60 ± 11.61 | 37.14 ± 17.21 | 75.62 ± 21.43 | 34.87***[a] ± 10.72 | 86.45 ± 15.34 |
| G4 | CYPRO-AF 100 mg/kg + High fat diet (with 60 kcal % Fat) | 6.27*[a] ± 0.31 | 3.08 ± 0.24 | 108.98 ± 34.03 | 41.86 ± 14.44 | 66.84 ± 5.55 | 44.60***[a] ± 14.87 | 84.90 ± 12.22 |

TABLE 10-continued

CLINICAL CHEMISTRY PARAMETERS IN FEMALE ANIMALS

| | | | | | | | | |
|---|---|---|---|---|---|---|---|---|
| G5 | CYPRO-AF 100 mg/kg + High fat diet (with 60 kcal % Fat) | 6.36 ± 0.37 | 2.99 ± 0.30 | 105.62 ± 27.44 | 35.78 ± 5.12 | 78.49 ± 10.08 | 39.31****$^a$ ± 8.30 | 105.15*$^a$ ± 14.39 |
| G6 | CYPRO-D1 10 mg/kg + High fat diet (with 60 kcal % Fat) | 6.73 ± 0.09 | 3.15 ± 0.32 | 110.20 ± 21.29 | 37.81 ± 18.55 | 68.87 ± 19.91 | 29.27****$^a$ ± 12.83 | 87.39 ± 17.68 |

| Group | Treatment | HDL (mg/dl) | VLDL (mg/dl) | LDL (mg/dl) |
|---|---|---|---|---|
| G1$^a$ | Control (with 10 kcal % Fat) | 14.70 ± 6.70 | 15.01 ± 2.28 | 42.01 ± 13.27 |
| G2$^b$ | High fat diet Control (with 60 kcal % Fat) | 20.48 ± 2.54 | 19.54 ± 2.18 | 47.61 ± 14.19 |
| G3 | CYPRO-AF 50 mg/kg + High fat diet (with 60 kcal % Fat) | 16.30**$^b$ ± 3.89 | 17.29 ± 3.07 | 47.80 ± 11.50 |
| G4 | CYPRO-AF 100 mg/kg + High fat diet (with 60 kcal % Fat) | 11.83***$^b$ ± 1.87 | 16.98 ± 2.44 | 54.19 ± 5.27 |
| G5 | CYPRO-AF 200 mg/kg + High fat diet (with 60 kcal % Fat) | 12.67***$^b$ ± 2.97 | 21.03*$^a$ ± 2.88 | 49.27 ± 4.39 |
| G6 | CYPRO-D1 10 mg/kg + High fat diet (with 60 kcal % Fat) | 9.91***$^b$ ± 1.90 | 17.48 ± 3.54 | 54.89 ± 13.74 | n = 5;
Values - Mean ± Standard Deviation;
P < 0.05

Clinical chemistry parameters statistical analysis comparison between G1 to G3, G4, G5, and G6

Total Proteins

In female animals, there was statistical significant decrease in mean Total protein values of G3 group {CYPRO-AF −50 mg/kg+High fat diet (with 60 kcal % Fat)} and G4 group {CYPRO-AF −100 mg/kg+High fat diet (with 60 kcal % Fat)} compared to G1 group {Control group (with 10 kcal % Fat)}. These changes were considered to be due to difference in fat content of the feed.

Triglycerides

In female animals, there was statistical significant decrease in mean Triglyceride values G3 group {CYPRO-AF −50 mg/kg+High fat diet (with 60 kcal % Fat)}, G4 group {CYPRO-AF −100 mg/kg+High fat diet (with 60 kcal % Fat)}, G5 group {CYPRO-AF −200 mg/kg+High fat diet (with 60 kcal % Fat)} and G6 group {CYPRO-D1 −10 mg/kg+High fat diet (with 60 kcal % Fat)} compared to G1 group {Control group (with 10 kcal % Fat)}. These change were considered to be due to difference in fat content of the feed.

Total Cholesterol

In male animals, there was statistical significant increase in mean Total Cholesterol value of G3 group {CYPRO-AF −50 mg/kg+High fat diet (with 60 kcal % Fat)} and G6 group {CYPRO-D1 10 mg/kg+High fat diet (with 60 kcal % Fat)} compared to G1 group {Control group (with 10 kcal % Fat)}. These change were considered to be due to difference in fat content of the feed.

In female animals, there was statistical significant increase in mean Total Cholesterol values of G5 group {CYPRO-AF−200 mg/kg+High fat diet (with 60 kcal % Fat)} compared to G1 group {Control group (with 10 kcal % Fat)}. This change can be considered due to difference in fat content of the feed.

High Density Lipids

In male animals, there was statistical significant decrease in mean High density lipids value of G5 group {CYPRO-AF−200 mg/kg+High fat diet (with 60 kcal % Fat)} compared to G1 group {Control group (with 10 kcal % Fat)}. This change can be considered due to difference in fat content of the feed.

Low Density Lipids

In male animals, there was statistical significant increase in mean Low density lipids value of G3 group {CYPRO-AF−50 mg/kg+High fat diet (with 60 kcal % Fat)}, G4 group {CYPRO-AF−100 mg/kg+High fat diet (with 60 kcal % Fat)} and G6 group {CYPRO-D1 −10 mg/kg+High fat diet (with 60 kcal % Fat)} compared to G1 group {Control group (with 10 kcal % Fat)}. These change were considered to be due to difference in fat content of the feed.

Very Low Density Lipids

In female animals, there was statistical significant increase in mean Very low density lipids value of G5 group {CYPRO-AF−200 mg/kg+High fat diet (with 60 kcal % Fat)} compared to G1 group {Control group (with 10 kcal % Fat)}. This change can be considered due to difference in fat content of the feed.

Clinical Chemistry Parameters Statistical Analysis Comparison Between G2 to G3, G4, G5, and G6

Triglycerides

In male animals, there was decrease in mean Triglycerides values of G3 group {CYPRO-AF 50 mg/kg+High fat diet (with 60 kcal % Fat)}, G4 group {CYPRO-AF–100 mg/kg+High fat diet (with 60 kcal % Fat)}, G5 group {CYPRO-AF 200 mg/kg+High fat diet (with 60 kcal % Fat)} and G6 group {CYPRO-D1 10 mg/kg+High fat diet (with 60 kcal % Fat)} compared to G2 group High fat diet Control (with 60 kcal % Fat). This decrease in mean Triglycerides values changes could be due the effect of the test items.

In female animals, there was statistical significant decrease in mean Triglycerides values of G6 group {CYPRO-D1 10 mg/kg+High fat diet (with 60 kcal % Fat)} compared to G2 group High fat diet Control (with 60 kcal % Fat). This decrease in mean Triglyceride values changes could be due the effect of the test items.

There was decrease in mean Triglyceride values of G3 group {CYPRO-AF 50 mg/kg+High fat diet (with 60 kcal % Fat)}, G4 group {CYPRO-AF 100 mg/kg+High fat diet (with 60 kcal % Fat)} and G5 group {CYPRO-AF 200 mg/kg+High fat diet (with 60 kcal % Fat)} compared to G2 group High fat diet Control (with 60 kcal % Fat). These decrease in mean Triglyceride values changes could be due the effect of the test items.

Total Cholesterol

In male animals, there was decrease in mean Total Cholesterol values of G3 group {CYPRO-AF 50 mg/kg+High fat diet (with 60 kcal % Fat)}, G4 group {CYPRO-AF–100 mg/kg+High fat diet (with 60 kcal % Fat)} and G5 group {CYPRO-AF 200 mg/kg+High fat diet (with 60 kcal % Fat)} compared to G2 group High fat diet Control (with 60 kcal % Fat). This decrease in mean Total Cholesterol values changes could be due the effect of the test items.

In female animals, there was decrease in mean Total Cholesterol values of G3 group {CYPRO-AF 50 mg/kg+High fat diet (with 60 kcal % Fat)}, G4 group {CYPRO-AF 100 mg/kg+High fat diet (with 60 kcal % Fat)}, and G6 group {CYPRO-D1 10 mg/kg+High fat diet (with 60 kcal % Fat)} compared to G2 group High fat diet Control (with 60 kcal % Fat). These decrease in mean Total Cholesterol values changes could be due the effect of the test items.

High Density Lipids

In male animals, there was statistical significant decrease in mean High density lipids values of G3 group {CYPRO-AF 50 mg/kg+High fat diet (with 60 kcal % Fat)}, G4 group {CYPRO-AF–100 mg/kg+High fat diet (with 60 kcal % Fat)}, G5 group {CYPRO-AF 200 mg/kg+High fat diet (with 60 kcal % Fat)} and G6 group {CYPRO-D1 10 mg/kg+High fat diet (with 60 kcal % Fat)} compared to G2 group High fat diet Control (with 60 kcal % Fat).

The statistical significant decrease in mean High density lipid values changes could be due the effect of the test items.

In female animals, there was statistical significant decrease in mean High density lipids values of G3 group {CYPRO-AF 50 mg/kg+High fat diet (with 60 kcal % Fat)}, G4 group {CYPRO-AF 100 mg/kg+High fat diet (with 60 kcal % Fat)}, G5 group {CYPRO-AF 200 mg/kg+High fat diet (with 60 kcal % Fat)} and G6 group {CYPRO-D1 10 mg/kg+High fat diet (with 60 kcal % Fat)} compared to G2 group High fat diet Control (with 60 kcal % Fat). These decreases in mean High density lipid values changes could be due the effect of the test items.

Low Density Lipids

In male animals, there was decrease in mean Low density lipids values of G5 group {CYPRO-AF 200 mg/kg+High fat diet (with 60 kcal % Fat)} compared to G2 group High fat diet Control (with 60 kcal % Fat). This decrease in mean Low density lipid values changes could be due the effect of the test items.

Very Low Density Lipids Values

In male animals, there was decrease in mean Very low density lipids values of G3 group {CYPRO-AF 50 mg/kg+High fat diet (with 60 kcal % Fat)}, G4 group {CYPRO-AF–100 mg/kg+High fat diet (with 60 kcal % Fat)}, 05 group {CYPRO-AF 200 mg/kg+High fat diet (with 60 kcal % Fat)} and G6 group {CYPRO-D1 10 mg/kg+High fat diet (with 60 kcal % Fat)} compared to G2 group High fat diet Control (with 60 kcal % Fat). This decrease in mean Very low density lipid values changes could be due the effect of the test items.

In female animals, there was marginal decrease in mean Very low density lipids values of G3 group {CYPRO-AF 50 mg/kg+High fat diet (with 60 kcal % Fat)}, G4 group {CYPRO-AF 100 mg/kg+High fat diet (with 60 kcal % Fat)}, and G6 group {CYPRO-D1 10 mg/kg+High fat diet (with 60 kcal % Fat)} compared to G2 group High fat diet Control (with 60 kcal % Fat). These decreases in mean Very low density lipid values changes could be due the effect of the test items.

Conclusion: From the present study, it can be concluded that the test items Cypro-AF and Cypro-D1 had an effect on decreasing parameters such as HDL, Triglycerides, Cholesterol, LDL and VLDL concentrations in high fat diet induced obese male and female C57 animals at 50, 100 and 200 mg/kg Bwt of Cypro-AF and 10 mg/kg Bwt of Cypro-D1. No significant statistical changes were observed in the organ weights and fat deposits upon necropsy of animals.

While the invention has been described with respect to a preferred embodiment it is to be clearly understood by those skilled in the art that the invention is not limited thereto. Rather, scope of the invention is to be interpreted only in conjunction with the appended claims.

We claim:

1. A method of reducing adipogenesis in mammalian cells, said method comprising step of bringing to contact adipogenic mammalian cells with compositions derived by the bioactivity guided fractionation of the ethyl acetate extract of *Cyperus rotundus* rhizomes said compositions consisting essentially of A: scirpusin A and scirpusin B represented by STR#1 and STR#2 respectively or B: piceatannol and its dimers scirpusin A and scirpusin B represented by STR#1 and STR#2 respectively, and measuring reduced adipogenesis in said cells using the Oil Red O staining technique.

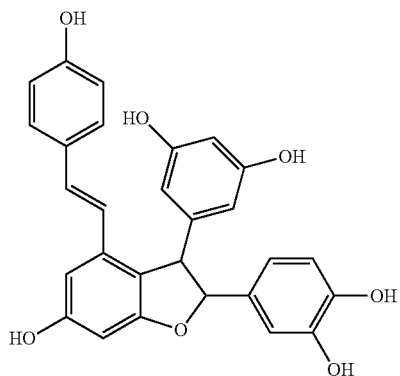

STR#1

-continued

STR#2

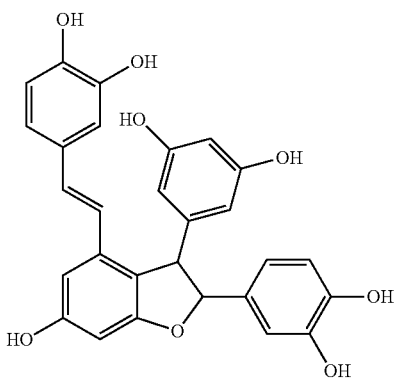

2. A method of therapeutically reducing obesity caused by high fat diet in mammals, said method comprising step of dietary supplementation of compositions derived by the bioactivity guided fractionation of the ethyl acetate extract of *Cyperus rotundus* rhizomes said compositions consisting essentially of A: scirpusin A and scirpusin B represented by STR#1 and STR#2 respectively or B: piceatannol and its dimers Scirpusin A and Scirpusin B represented by STR#1 and STR#2 respectively, to said mammals to bring about the effect of reduction in body weight.

STR#1

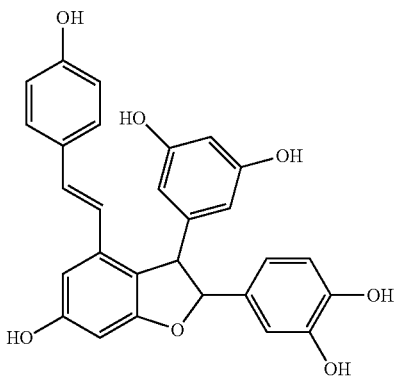

STR#2

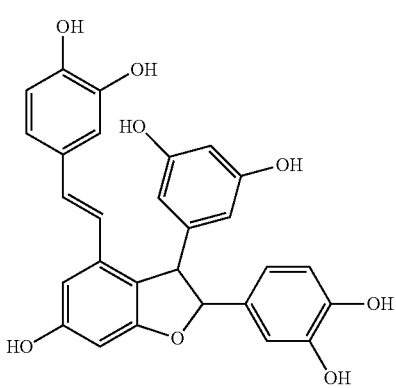

3. A method of reducing adipogenesis in adipogenic mammalian cells comprising administering compositions derived by the bioactivity guided fractionation of the ethyl acetate extract of *Cyperus rotundus* rhizomes said compositions consisting essentially of A: scirpusin A and scirpusin B represented by STR#1 and STR#2 respectively or B: piceatannol and its dimers Scirpusin A and Scirpusin B represented by STR#1 and STR#2 respectively for reducing adipogenesis in mammalian cells said method comprising step of treating adipogenic mammalian cells (mammalian adipocytes) with effective concentration of said compositions to achieve the effect of reduction in adipogenesis.

STR#1

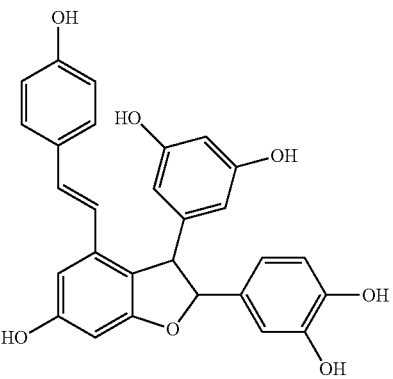

STR#2

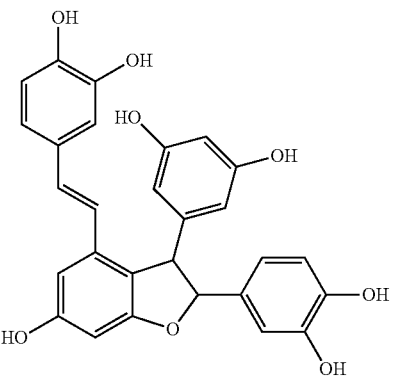

4. A process for the bioactivity guided fractionation of the rhizomes of *Cyperus rotundus* to obtain anti-adipogenic/anti-obesity compositions comprising A: scirpusin A and scirpusin B represented by STR#1 and STR#2 and B: piceatannol and its dimers scirpusin A and scirpusin B represented by STR#1 and STR#2 respectively, said process comprising the steps of:
1—Drying the rhizomes of *Cyperus rotundus* and pulverizing the same to form a coarse powder;
2—Extracting the powder of step 1 with 3 volumes of hexane followed by heating, reflux for 3 hours and filtering to obtain the hexane soluble fraction and spent material;
3—Extracting the spent material of step 2 with 3 volumes of methanol followed by heating, reflux for 3 hours and filtering to obtain the methanol soluble active fraction and spent material;
4—Solubilizing the methanol soluble active fraction of step 3 in aqueous methanol and successively partitioning with chloroform (CHCl$_3$), Ethyl acetate (EtOAc) and methanol to obtain the chloroform layer, ethyl acetate layer and aqueous methanol layer respectively;

5—Subjecting the chloroform layer, ethyl acetate layer and the aqueous methanol layer to further bioactivity guided fractionation, wherein the bioactivity parameter is the ability of the chloroform layer, ethyl acetate layer and the aqueous methanol layer to inhibit adipogenesis in 3T3-L1 mouse adipocytes (mammalian adipocytes);

6—Calculating the $IC_{50}$ (μg/ml) values for adipogenesis inhibition exemplified by chloroform layer, ethyl acetate layer and the aqueous methanol layer (0, 9.39 and 66.42 respectively);

7—Fractionation of the ethyl acetate layer using column fractionation to identify the bioactivity (adipogenesis inhibition) biomarker, said fractionation includes the step where fractions are eluted with increasing polarity of methanol: chloroform to yield sub fractions of the ethyl acetate layer (fraction);

8—Subjecting the sub fractions of step 7 for bioactivity (anti-adipogenesis) analysis;

9—Identifying the most bioactive sub fractions of step 8 and subjecting the same to LC-MS analysis to identify the bioactive principles scirpusin A and scirpusin B; and 10—Subjecting sub fractions of step 7 through the preparative HPLC to obtain purified dimer and subjecting the same to High Resolution Mass Spectroscopy (HRMS), liquid chromatography-mass spectrometry (LC-MS/MS) and Nuclear Magnetic Resonance Spectroscopy (NMR) to confirm the mass and structures of scirpusin bioactive principles.

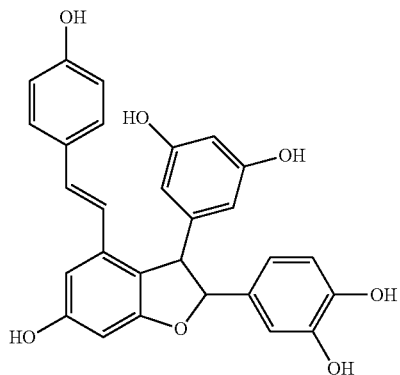

STR#1

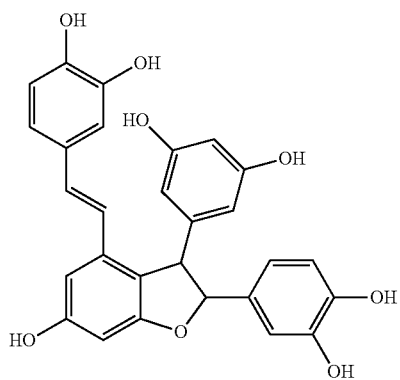

STR#2

* * * * *